United States Patent
Scheurer et al.

(10) Patent No.: US 12,403,264 B2
(45) Date of Patent: Sep. 2, 2025

(54) DOSING SYSTEM FOR AN INJECTION DEVICE

(71) Applicant: Ypsomed AG, Burgdorf (CH)

(72) Inventors: Simon Scheurer, Bern (CH); Patrick Hostettler, Hasle (CH); Jürg Hirschel, Bern (CH)

(73) Assignee: Ypsomed AG, Burgdorf (CH)

( * ) Notice: Subject to any disclaimer, the term of this patent is extended or adjusted under 35 U.S.C. 154(b) by 844 days.

(21) Appl. No.: 17/467,908

(22) Filed: Sep. 7, 2021

(65) Prior Publication Data

US 2021/0393885 A1 Dec. 23, 2021

Related U.S. Application Data

(63) Continuation of application No. PCT/EP2020/055385, filed on Mar. 2, 2020.

(30) Foreign Application Priority Data

Mar. 15, 2019 (EP) ..................... 19163197

(51) Int. Cl.
*A61M 5/315* (2006.01)

(52) U.S. Cl.
CPC ...... *A61M 5/31551* (2013.01); *A61M 5/3157* (2013.01); *A61M 5/31585* (2013.01);
(Continued)

(58) Field of Classification Search
CPC ...... A61M 2205/581; A61M 2205/582; A61M 5/31501; A61M 5/315; A61M 5/31525;
(Continued)

(56) References Cited

U.S. PATENT DOCUMENTS

| 2015/0051551 A1* | 2/2015 | Hirschel ........... A61M 5/31551 604/207 |
| 2015/0088079 A1 | 3/2015 | Butler et al. |

(Continued)

FOREIGN PATENT DOCUMENTS

| EP | 1003581 A1 | 5/2000 |
| EP | 2262533 A1 | 12/2010 |

(Continued)

OTHER PUBLICATIONS

English translation of International Search Report issued in International Application No. PCT/EP2020/055385, mailed on Mar. 31, 2020, 3 pages.

(Continued)

*Primary Examiner* — Lauren P Farrar
*Assistant Examiner* — Guillermo G Paz Estevez
(74) *Attorney, Agent, or Firm* — Dorsey & Whitney LLP

(57) ABSTRACT

A dosing system for an injection device for dispensing a dose of a product includes a housing having a longitudinal axis, a dose-setting element, a holding element and a coupling sleeve for driving a driving device for dispensing the dose. The dose-setting element, holding element, and coupling sleeve may be accommodated in the housing. To set and correct the dose, the dose-setting element and the coupling sleeve move in the direction of the longitudinal axis relative to the housing, and the coupling sleeve may be held the holding element rotationally fixed by relative to the housing. To dispense the dose, the coupling sleeve may rotate relative to the housing, the dosing system including a guide in the housing, in which guide the holding element may be displaced in the direction of the longitudinal axis relative to the housing and be guided in a rotationally fixed manner relative to the housing.

19 Claims, 10 Drawing Sheets

(52) U.S. Cl.
CPC ..... *A61M 5/31528* (2013.01); *A61M 5/31533* (2013.01); *A61M 5/31548* (2013.01); *A61M 2205/581* (2013.01); *A61M 2205/582* (2013.01)

(58) Field of Classification Search
CPC .......... A61M 5/31533; A61M 5/31548; A61M 5/3155; A61M 5/31528; A61M 5/31541; A61M 5/31551; A61M 5/3157; A61M 5/31585; A61M 5/31593; A61M 5/32
See application file for complete search history.

(56) References Cited

U.S. PATENT DOCUMENTS

| | | | |
|---|---|---|---|
| 2015/0112274 A1* | 4/2015 | Quinn | A61M 5/31585 604/207 |
| 2017/0319789 A1 | 11/2017 | Veasey et al. | |

FOREIGN PATENT DOCUMENTS

| | | |
|---|---|---|
| EP | 3708206 A1 | 9/2020 |
| WO | 2020187547 A1 | 9/2020 |

OTHER PUBLICATIONS

International Preliminary Report on Patentability received for International Application No. PCT/EP2020/055385, mailed on Sep. 16, 2021, 8 pages, Sep. 16, 2021.

* cited by examiner

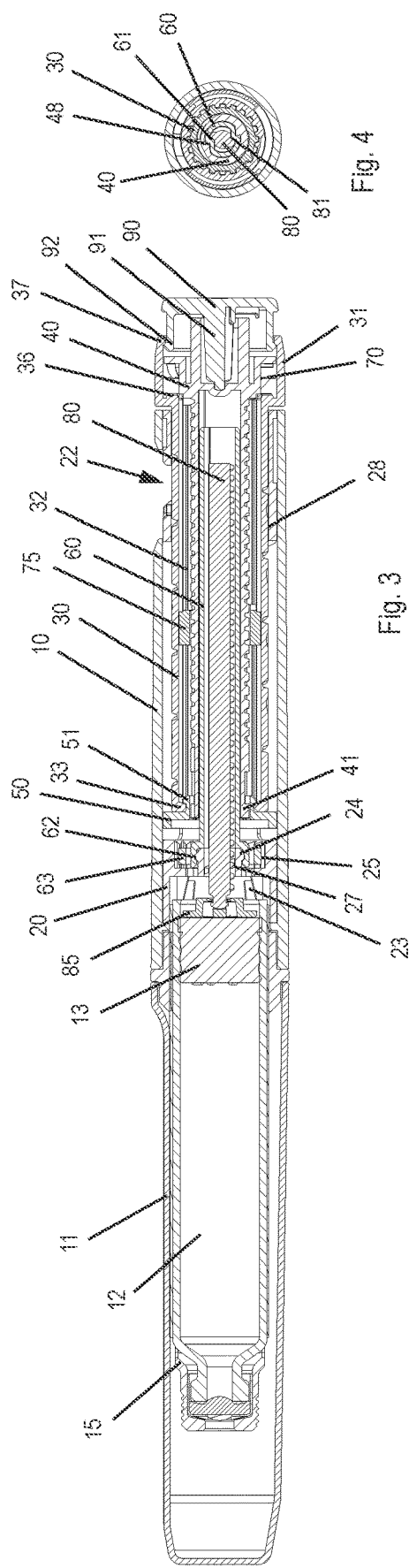
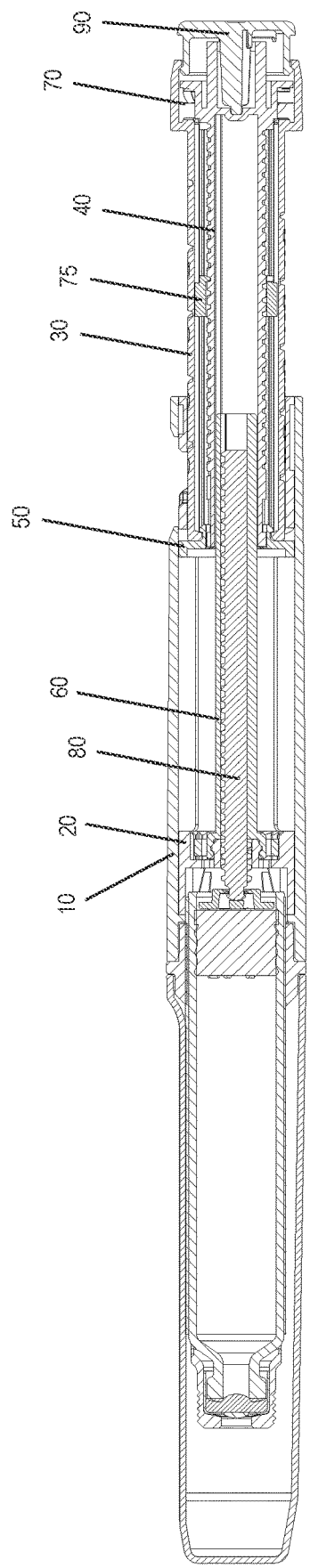

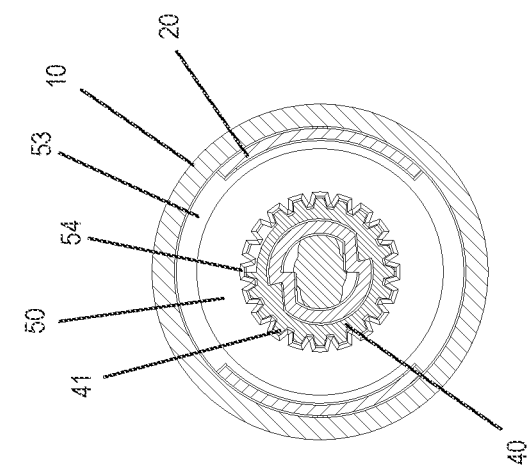
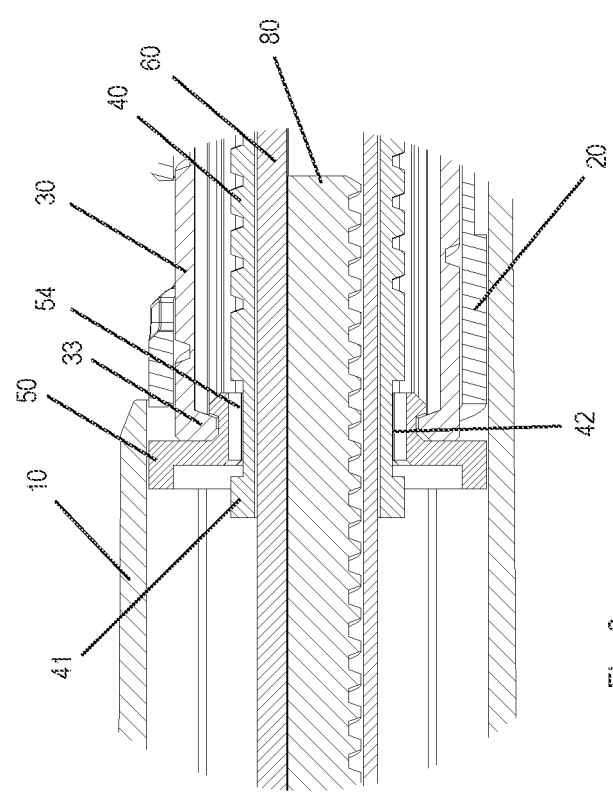
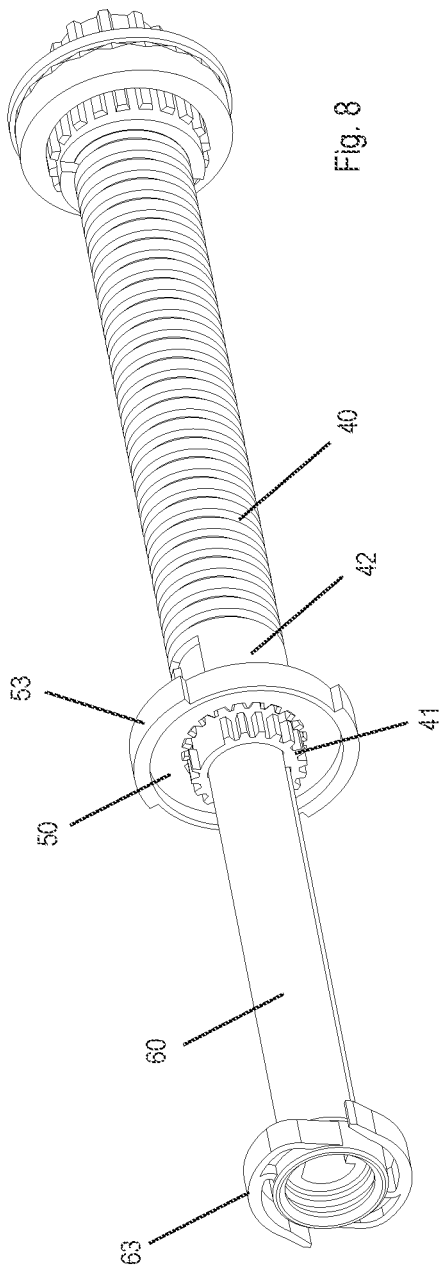
Fig. 7
Fig. 6
Fig. 8

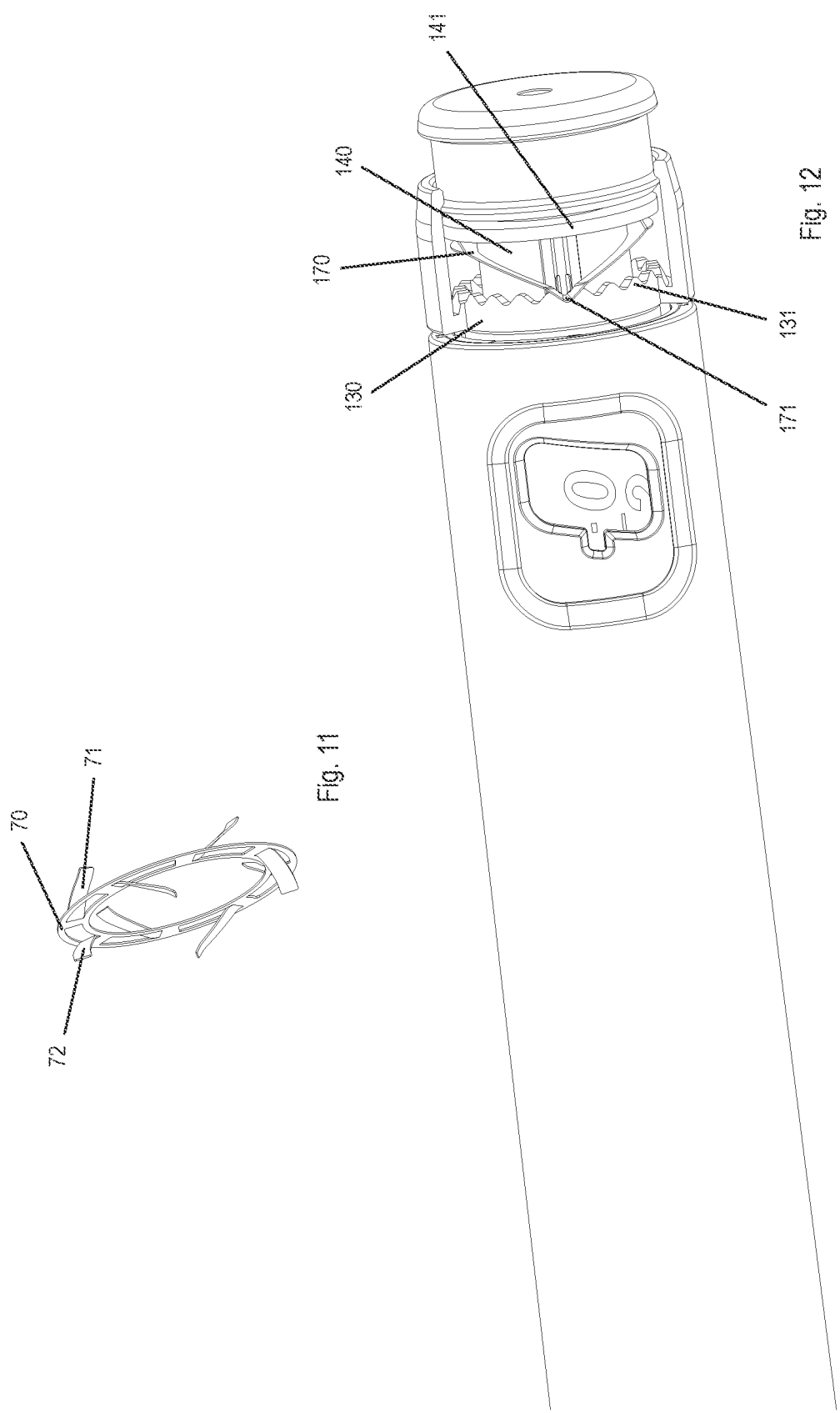

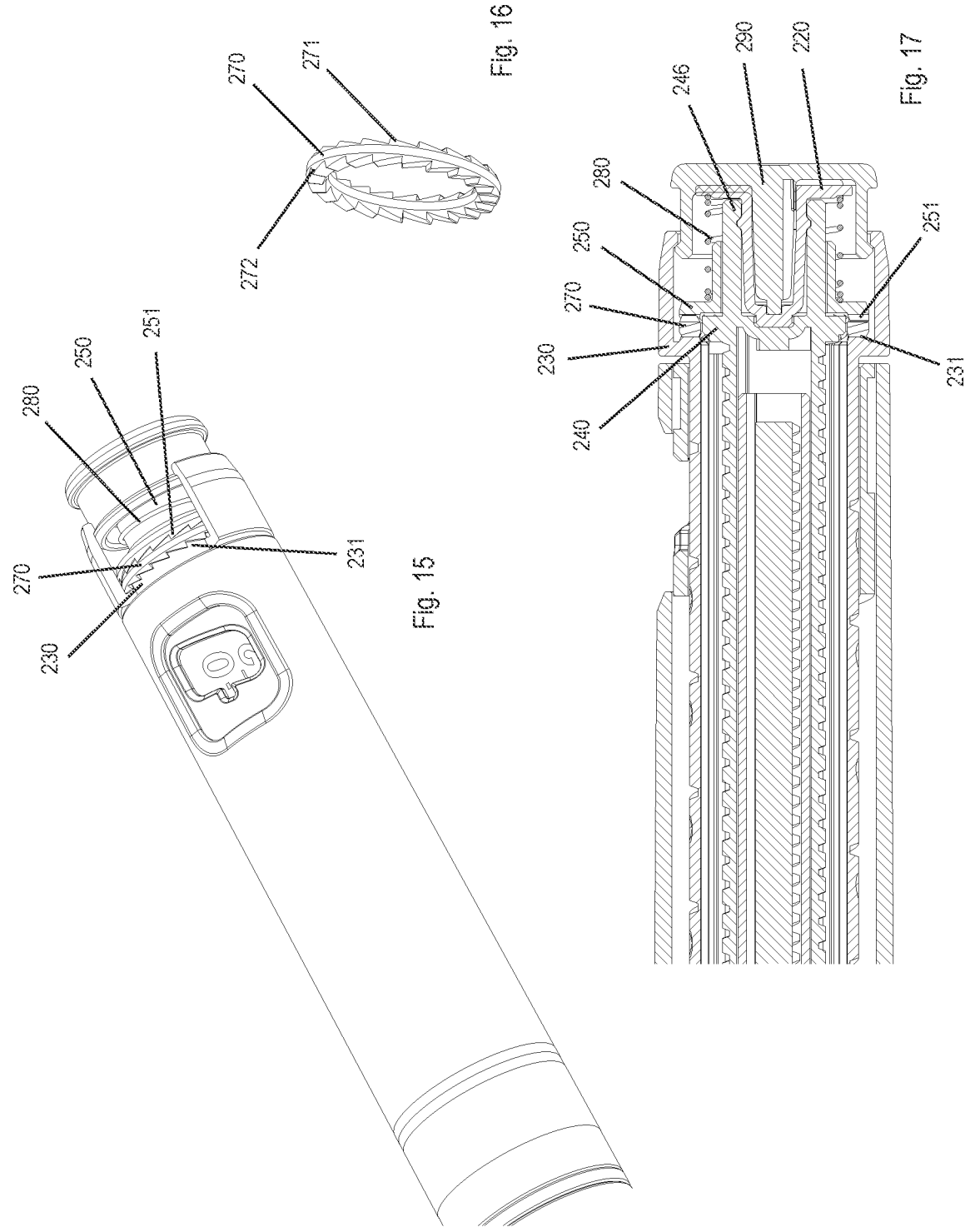

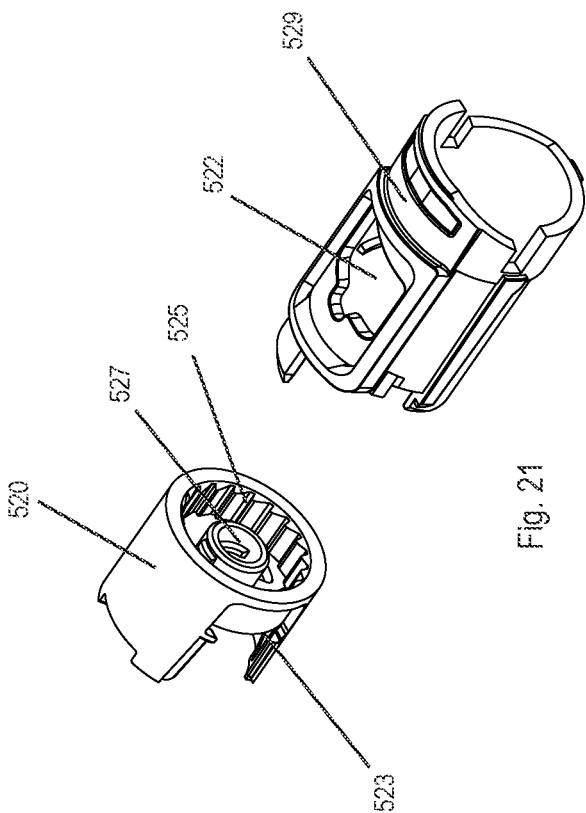
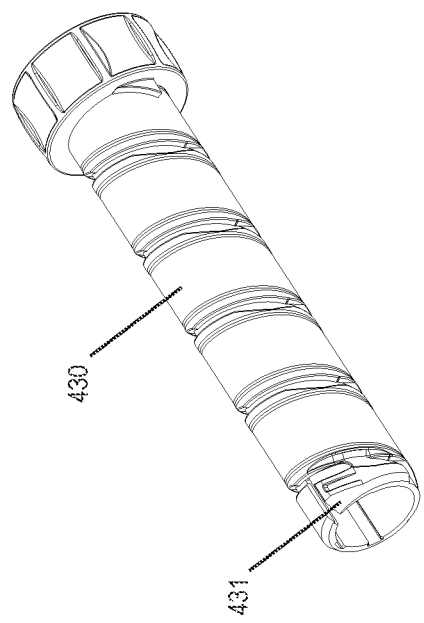
Fig. 21
Fig. 20

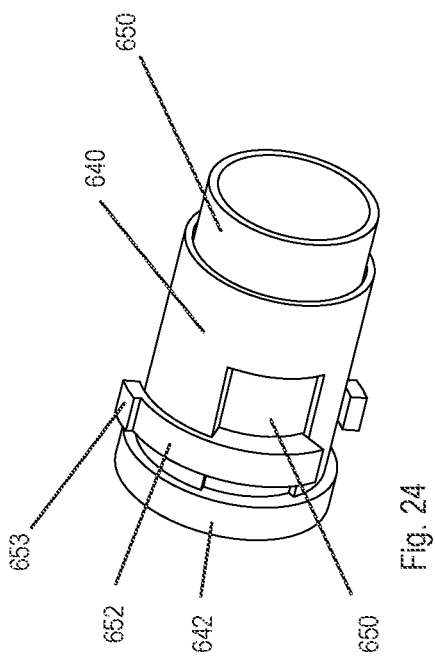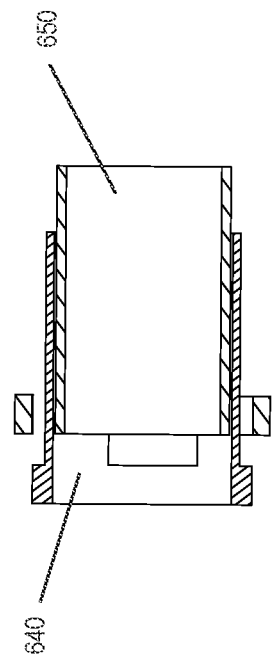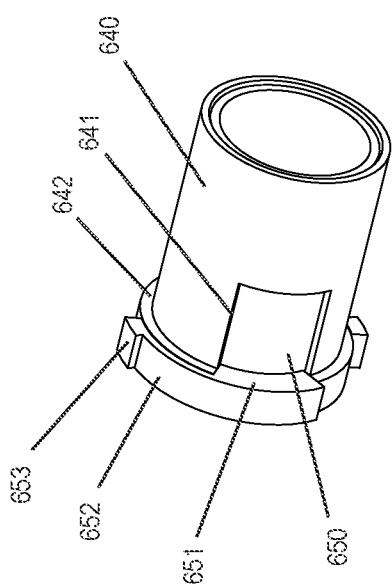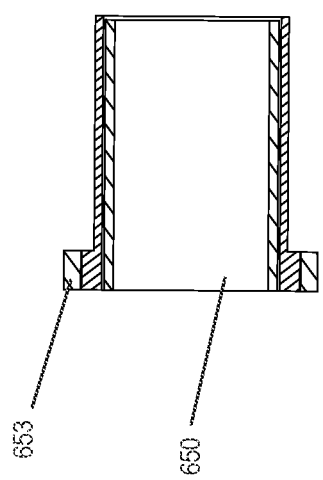

DOSING SYSTEM FOR AN INJECTION DEVICE

CROSS REFERENCE TO RELATED APPLICATIONS

This application claims priority to International Patent Application No. PCT/EP2020/055385, filed Mar. 2, 2020, entitled "DOSING SYSTEM FOR AN INJECTION DEVICE," which in turn claims priority to European Patent Application No. 19163197.7, filed Mar. 15, 2019, entitled "DOSING SYSTEM FOR AN INJECTION DEVICE", each of which is incorporated by reference herein, in the entirety and for all purposes.

TECHNICAL FIELD

Implementations are directed to the field of medical injection apparatuses for administering liquid substances, such as medications or medical substances including insulin and hormone preparations, and more particularly relate to a dosing device for an injection apparatus that may include a dose setting element for setting a dose and a coupling sleeve for releasably coupling the dose setting element to a drive device to dispense the dose.

BACKGROUND

Known injection apparatuses typically comprise a drive sleeve for driving a piston rod to dispense the liquid substance from a carpule or a product container, a dosing sleeve for setting a dose to be administered, and a coupling sleeve for either directly or indirectly coupling the dosing sleeve to the drive sleeve.

In order to set a dose to be administered, the user turns or pulls on the dosing sleeve, which is rotated out of or moved out of the housing of the injection apparatus. So that the set dose can be dispensed, e.g., injected, the user presses a release button at a proximal end of the injection apparatus or generates a force in the distal direction, thereby rotating (e.g., screwing) or pushing the dosing sleeve into the housing. Rather than setting a dose, the coupling sleeve, at the moment of dispensing, in contrast transmits the rotary or sliding movement of the dosing sleeve to the drive sleeve, which thereby drives the piston rod and dispenses the substance. Depending on the configuration of the injection apparatus, the piston rod can be rotated, or simply displaced relative to the housing.

In order to correct a dose that has inadvertently been set too high, the user can screw or slide the dosing sleeve back into the housing. During this corrective movement, as well as when the injection apparatus is handled between administrations, it must be ensured that the position of the piston rod cannot be unintentionally moved relative to the carpule—in particular, it must be ensured that the piston rod does not move away from the carpule.

One way to prevent unintentional movement is to use what is known as a reverse rotation lock or an anti-rotation lock. This either directly prevents the rotation of the piston rod opposite the direction of rotation for dispensing the substance, or it engages the driving element, such that a return movement of the piston rod is indirectly prevented. The latter has the advantage that the anti-rotation lock can also be used with piston rods which exclusively perform a pushing movement for the administration.

A pen-shaped injection apparatus having a dosing device with the afore-mentioned arrangement, with a dosing and coupling sleeve, is described, for example, in EP 1 003 581 B1. The housing of the injection apparatus has an internal thread into which the piston rod is screwed. After the dose is set, the dosing sleeve is pressed into the housing by means of a button. As a result, the coupling sleeve situated in the dosing sleeve is coupled to the dosing sleeve, such that the rotary movement is transmitted to the drive sleeve arranged coaxially within the coupling sleeve. The drive sleeve is axially fixed in the housing. With its rotary movement, the piston rod screws through the internal thread. As a result, a flange at the end of the piston rod is pressed against a stopper in a carpule, such that the product is dispensed from the carpule. The drive sleeve has radially protruding arms which cooperate with saw teeth fixed to the housing, thereby forming a ratchet. Due to the saw tooth shape, the arms can only be moved over the teeth in one direction, and lock in the opposite direction. A reverse rotation lock is thus implemented, in which the drive sleeve and thus the piston rod can only be rotated in the dispensing direction.

With this configuration of the reverse rotation lock, the arms of the drive sleeve must be pressed against the saw teeth with a biasing force so that the reverse rotation lock can function, and so that the drive sleeve cannot nevertheless be rotated in the opposite direction. Biasing has the consequence that the friction during the rotary movement upon dispensing means that an increased force or an increased rotary torque has to be applied.

EP 2 262 533 B1 discloses a further possibility of a reverse rotation lock. The injection apparatus described is a so-called autopen, in which the plunger rod for the dispensing is not driven by a force applied by the user, but rather by a spring force generated by a preloaded spring. The drive sleeve which drives the piston rod has a cam which engages in a locking sleeve. As a result, the locking sleeve holds the drive sleeve in a rotationally fixed manner relative to the housing. The locking sleeve is mounted in a rotationally fixed but axially displaceable manner relative to the housing. To dispense the dose, the locking sleeve is pushed in the axial direction relative to the drive sleeve over the cam, thereby releasing the rotation of the drive sleeve, such that the drive sleeve can rotate, driven by the preloaded spring, and can drive the piston rod for the dispensing.

This construction is limited to spring-driven injection apparatuses in which no dosing sleeve has to be moved in the axial direction relative to the housing in order to set a dose. For injection apparatuses with a dosing sleeve, as described, for example, in the afore-mentioned EP 1 003 581 B1, such a reverse rotation lock with a locking sleeve does not work, since the dosing sleeve is displaced relative to the housing when a dose is set and/or dispensed.

SUMMARY

Implementations provide injection apparatuses configured for setting a dose that include a dose setting element that may be displaced relative to a housing of the injection apparatus, while minimizing the expenditure of force for the dispensing the dose.

This object may be achieved by providing a dosing device and an injection apparatus according to the disclosed implementations. The dosing device may include a housing with a longitudinal axis, a dose setting element for setting the dose, a holding element, and a coupling sleeve for driving a drive device to dispense the dose. The dose setting element, the holding element and the coupling sleeve may be arranged in the housing. To set and correct the dose, the dose setting element and the coupling sleeve may be displaced relative to the housing, and the coupling sleeve may be held in a rotationally fixed manner relative to the housing, for instance by means of the holding element. To dispense the dose, e.g., during an injection, the coupling sleeve may be released by the holding element, such that the coupling sleeve may rotate relative to the housing, where the dosing device in the housing may include a guide in which the holding element may be displaced in the direction of the longitudinal axis relative to the housing, for instance when setting and correcting a dose, and may be guided in a rotationally fixed manner relative to the housing. "Rotationally fixed" means that no relative rotation is possible. The guide may be formed by the housing itself or by an element within the housing.

As the holding element may be axially displaceable in the guide of the housing (that is, in the direction of the longitudinal axis of the housing) relative to the housing, the holding element may move axially together with the coupling sleeve when a dose is set or corrected. However, at every axial position, the coupling sleeve may be held in a rotationally fixed manner relative to the housing by means of the holding element. As a result, any torque may be transmitted directly to the housing, or supported on it. Thus the coupling sleeve may be prevented from rotating relative to the housing during setting and correction, and as a result of which, the drive device may not be driven. This may efficiently prevent the product from being dispensed unintentionally. The holding element may selectively hold the coupling sleeve relative to the housing or may permit the rotation of the coupling sleeve relative to the housing so that the coupling sleeve may drive the drive device and thus dispense the substance from the carpule or the product container.

During dispensing, the coupling sleeve may be released by the holding element, such that the coupling sleeve may be rotated relative to the housing. The holding element may not operate together with the coupling sleeve during dispensing, and may not influence the coupling sleeve when the coupling sleeve rotates. A reverse rotation lock on a drive sleeve, for instance as known from prior approaches, which may cause increased friction during the dispensing rotation, may thus be avoided. The dosing device according to the disclosed implementations may thus enable a reverse rotation lock without additionally increasing friction during dispensing, and thus may not influence the amount of force required for dispensing.

For instance, relative to prior approaches, to prevent reverse rotation, there may be no need to use any manner of a ratchet having radial, flexible arms on the drive sleeve, such as is disclosed in EP 2 262 533 B1. Such a ratchet may instead be used to generate an acoustic or tactile signal for instance as feedback for the user. As a result, for example, the flexible arms of the ratchet may be pressed onto the teeth of the ratchet with less preloading, and the effort required during dispensing to overcome the friction may be considerably reduced.

Implementations further provide an injection apparatus including a carpule holder for holding a carpule with a medical substance and the dosing device. The injection apparatus may be an injection pen, such as a disposable injection pen. For instance, the injection apparatus may include a carpule holder for holding a carpule with the medical substance, a needle or cannula that may be attached to the carpule holder so that the medical substance can be administered through the needle or cannula, the dosing device, and the drive device with a piston rod, which is described in detail in the following disclosure. In the injection apparatus, the dose to be administered may be set using the dose setting element. The dose or doses may be provided in one or more injections until all of the product present in the injection apparatus has been dispensed. The injection apparatus may be configured in the shape of a pen with an elongated housing, such as a cylindrical housing which, however, may not necessarily have a circular cross-section, and may for instance have an oval or a polygonal cross-section. The coupling sleeve may be arranged coaxially in the housing. For instance, the coupling sleeve may have an elongated, cylindrical shape. The holding element may be located between an inner wall of the housing and an outer side of the coupling sleeve. The holding element may also be arranged coaxially in the housing and may, for example, be sleeve-shaped or ring-shaped. The holding element may alternatively be configured in the form of a disk, an insert, or in the form of an arm which may be oriented in the radial direction and which may hold the coupling sleeve in a rotationally fixed manner relative to the housing.

The dose setting element, the holding element and the coupling sleeve may be located within the housing of the dosing device. However, this should not preclude individual elements or regions of the dose setting element, the coupling sleeve, and the holding element from protruding from the housing. For instance, a proximal end region of the dose setting element and the coupling sleeve may be located outside the housing.

The injection apparatus may include a product container, such as a carpule, in which a medical substance is found. In order to dispense the product from the product container, a stopper in the product container may be pushed in a dispensing direction in the distal direction, for example, by means of a piston rod of the injection apparatus. This dispensing direction may be parallel to the direction of the longitudinal axis of the housing.

In some implementations, the housing may further include a housing insert, which may be configured in the form of a sleeve and may be arranged in the housing coaxially with the central longitudinal axis of the housing. The housing insert may, for example, rotatably support elements of the drive device, for example a drive sleeve. The guide for the holding element may be formed, for example, in the housing, in the housing insert, in other elements in the housing, or partially in the housing and partially in the housing insert.

The drive device may serve to dispense the product from the product container. In some implementations, the drive device may include a drive sleeve and a piston rod. The drive sleeve may drive the piston rod in the distal direction, and may move the stopper in the product container in order to dispense the product. The coupling sleeve may drive the drive sleeve. In this case, the drive sleeve may only be mounted in the housing in a manner allowing sliding, allowing rotation, or allowing sliding and rotation, for instance by a screwing motion, in order to drive the piston rod. For dispensing the product, the drive sleeve may be moved or only displaceably mounted in the housing by means of a screwing motion.

In some implementations, the drive sleeve may be held in a rotationally fixed but axially displaceable manner relative to the piston rod, and the piston rod may be arranged within the drive sleeve. The drive sleeve may be mounted to be rotatable relative to the housing, but may be prevented from being displaced relative to the housing in the longitudinal direction of the housing.

During the setting, correcting and dispensing of the dose, e.g., during injection, the coupling sleeve may be displaceable in the axial direction relative to the housing and relative to any housing insert that may be present. Furthermore, by means of the holding element, the coupling sleeve may be selectively rotationally fixed or free to rotate relative to the housing. Furthermore, the coupling sleeve may be arranged inside the housing and may surround the elements of the drive device, such as a drive sleeve. In some implementations, the coupling sleeve may be displaced in the longitudinal direction of the housing relative to the drive device. As a result, the coupling sleeve may interact or couple with the drive device at different axial positions.

If the dispensing process is triggered, e.g., during an injection into a user or patient, for example by the coupling sleeve being moved relative to the holding element directly, or indirectly via a further element, the coupling sleeve may be released by the holding element. The coupling sleeve may then be guided back into the housing, for example by means of a rotational movement or screwing movement, and may interact or couple with the drive device via a rotation or displacement relative to the housing, such that the product can be dispensed.

The holding element may be displaced in the direction of the longitudinal axis of the housing, relative to the housing, in the guide in the housing, in a potentially-present housing insert, or in some other element within the housing, but in any case may be guided in a rotationally fixed manner relative to the housing. The holding element may be displaceable in the direction of the longitudinal axis both when setting and correcting a set dose, as well as during the dispensing of a set dose. Furthermore, the holding element may be held in a rotationally fixed manner relative to the housing by means of the guide or by means of additional elements, such as by a tooth, cam or web in the holding element and a complementary-shaped groove or recess extending in the axial direction in the housing or in the housing insert. Alternatively, the housing, a housing insert, or some other element fixed to the housing may include a tooth, cam or web, and the holding element may include a correspondingly shaped groove or recess.

In some implementations, during the setting and the correction of a dose, the coupling sleeve may be held in a rotationally fixed manner relative to the housing by a toothed engagement between the coupling sleeve and the holding element. To dispense the dose, the coupling sleeve may be displaced relative to the holding element in the direction of the longitudinal axis, such that the toothed engagement between the coupling sleeve and the holding element may be overridden, and the coupling sleeve may rotate relative to the housing.

During the setting and correction of the dose, the holding element may hold the coupling sleeve, for instance by an engagement element, a toothed engagement, or a force-fit connection. During dispensing, however, the coupling sleeve may be released by the holding element. Thus, the coupling sleeve may not be held on the holding element, and the coupling sleeve may move relative to the housing. For example, the engagement element may no longer be in an engagement, or the friction-fit connection may be released.

The coupling sleeve may include an engagement element, and the holding element may include a counter-engagement element, and the engagement element and the counter-engagement element may be configured to engage with each other to rotationally couple the coupling sleeve and the holding element. As a result, when engaged, the coupling sleeve may also be held in a rotationally fixed manner relative to the housing.

The engagement element and the counter-engagement element may, for example, each be formed by at least two teeth which may be configured to mesh with each other. However, the engagement element and counter-engagement element may also be implemented as a projection (cam, web, rib) and a groove that receives the projection. In this case, the coupling sleeve may either be configured as a projection or a groove, and the holding element may be configured as the other of the two.

The dose setting element may be moved relative to the housing in the direction of the longitudinal axis. The dose setting element may also be rotatable relative to the housing, or rotatable and displaceable relative to the housing, for instance by a screwing movement. The dose setting element may, for example, be ring-shaped, sleeve-shaped, or shell-shaped. Furthermore, the dose setting element may also be configured as an axial slide to position the coupling sleeve in the axial direction as a function of the dose. Furthermore, the dose setting element may be configured as a rotatable and axially displaceable knob, handle, as a sleeve, or as a button. In some implementations, the dose setting element may be configured as a dosing sleeve which may be arranged in the housing coaxially with the longitudinal axis of the housing.

In some implementations, for setting and correcting a dose, the dose setting element and the coupling sleeve may be decoupled from each other such that the dose setting element may move relative to the coupling sleeve. To dispense the dose, the dose setting element and the coupling sleeve may be coupled to each other such that the dose setting element is prevented from moving relative to the coupling sleeve.

When changing from setting and correcting the dose (a) to dispensing the dose (b), the coupling sleeve may be released by the holding element and then, after the coupling sleeve is released, the coupling sleeve may be coupled to the dose setting element. In a further embodiment, however, the coupling sleeve may be released by the holding element and may be coupled to the dose setting element at the same time, e.g., simultaneously. In a third embodiment, however, the coupling sleeve which may be held non-rotatably relative to the housing by means of the holding element may also first be coupled to the dose setting element, and only then may the coupling sleeve be released by the holding element.

The term "distal" denotes a frontal end of the injection apparatus where piercing occurs, and/or a side or direction towards the tip of the injection needle. In contrast, the term "proximal" denotes a side or direction towards the rear end of the injection apparatus opposite the end where the piercing occurs.

The term axial refers to the longitudinal axis of the housing. Correspondingly, an axial direction is parallel to the longitudinal axis of the housing or in the longitudinal direction of the housing. A radial direction refers to a direction perpendicular to the longitudinal axis of the housing.

The term "product," "medication" or "medicinal substance" in the present disclosure includes any flowable medical formulation which may be suitable for controlled administration by means of a cannula or hollow needle into subcutaneous or intramuscular tissue, for example a liquid, a solution, a gel or a fine suspension containing one or more medicinal active ingredients. As such, a medication may be a single agent composition or a premixed or co-formulated multiple agent composition from a single container. The term includes drugs such as peptides (e.g. insulins, drugs containing insulin, preparations containing GLP 1, or derived therefrom or analogous thereto), proteins and hormones, biologically obtained or active substances, substances based on hormones or genes, nutritional formulations, enzymes and other substances in solid (suspended) or liquid form. The term also includes polysaccharides, vaccines, DNA or RNA or oligonucleotides, antibodies or parts of antibodies as well as suitable base, adjuvant, and carrier sub stances.

The terms "injection apparatus" or "injector" in the present disclosure are understood to mean a device in which the injection needle is removed from the tissue after a controlled amount of the medical substance has been dispensed. As such, in the case of an injection system or an injector, in contrast to an infusion system, the injection needle does not remain in the tissue for a prolonged period of several hours.

According to implementations, by moving the coupling sleeve relative to the holding element in the direction of the longitudinal axis of the housing, the coupling sleeve may be rotationally released by the holding element for the dispensing operation, such that the coupling sleeve may rotate relative to the housing. For instance, the drive device may be driven by the rotating coupling sleeve, and the set dose may be dispensed. The term "displacement" is understood to mean a movement along a linear, straight or curved, but not circular, path. Accordingly, a displacement is different from a rotation. With the latter, the movement takes place along a circle. In turn, a "linear path" is understood to mean a line that is continuously differentiable.

Because the coupling sleeve can be displaced, the coupling sleeve may be decoupled quickly and easily from the holding element, for example if the user activates the dispensing of the dose by actuating a release button.

Alternatively, the coupling sleeve may be released by the holding element by means of relative rotation or, for example, by radial engagement elements of the coupling sleeve being released from engagement with the holding element in the radial direction, such that the coupling sleeve can be rotated relative to the holding element.

The coupling sleeve may also be coupled to the dose setting element in a rotationally fixed manner by the displacement of the coupling sleeve. In this context, "coupleable" means that the coupling sleeve may be releasably connected to the dose setting element. The coupling may therefore be released again at any time in that the coupling sleeve may be decoupled from the dose setting element, such that the coupling sleeve may rotate again relative to the dose setting element.

The relative displacement of the coupling sleeve with respect to the holding element may thus cause, on the one hand, the rotational release (or decoupling) of the coupling sleeve from the holding element and, on the other hand, the rotational coupling of the coupling sleeve to the dose setting element. After the displacement, the coupling sleeve may thus be held rotatably relative to the holding element but non-rotatably relative to the dose setting element. Thus, two couplings may be switchable with a single displacement movement of the coupling sleeve.

After the coupling sleeve has been coupled to the dose setting element, a movement, such as a screwing movement, of the dose setting element may be transmitted to the coupling sleeve.

The coupling sleeve may be coupled to the dose setting element in a rotationally fixed manner by means of a toothed engagement. As a result, a rotational torque may be safely and reliably transmitted from the dose setting element to the coupling sleeve, and vice versa.

As mentioned, the term "coupleable" means that the connection can be released. The term "toothed engagement" is not limited to a connection with two intermeshing teeth, but includes any connection with engagement elements in which a force can be transmitted by means of a friction fit. For example, the coupling sleeve or the dose setting element can have engagement elements in the form of cams, prongs, tines, projections, wedges, pins or other formations, which can engage in correspondingly shaped grooves, depressions, recesses, holes or counter-engagement elements in the counterpart, i.e., in the dose setting element or in the coupling sleeve, such that the coupling sleeve and dose setting element may be prevented from rotating relative to each other.

The dose setting element may include at least one groove oriented in the direction of the longitudinal axis, and the coupling sleeve may have at least one radial cam which may engage in the at least one groove, such that the coupling sleeve may be coupled easily and securely to the dose setting element in a rotationally fixed manner. In some implementations, this coupling may be established by moving the coupling sleeve relative to the dosing sleeve and the at least one cam may be inserted into the at least one groove in the direction of the longitudinal axis.

In an alternative embodiment, the coupling sleeve may be connected to the dose setting element in a rotationally fixed manner by means of a force fit, for example, by means of a conical connection (conical pin and conical bore).

In some implementations, the coupling sleeve may be held in a rotationally fixed manner relative to the holding element for example by a toothed engagement. As a result, the coupling sleeve may be held securely and reliably against rotation relative to the holding element. Since the holding element may also be held in a rotationally fixed manner relative to the housing, the coupling sleeve may be securely held in a rotationally fixed manner relative to the housing.

As provided herein, the term "toothed engagement" does not only refer to teeth, but includes all engagement elements that can be brought into engagement with each other.

The toothed engagement may be configured with at least one cam and at least one groove. In this case, the holding element may include at least one groove oriented in the direction of the longitudinal axis of the housing, and the coupling sleeve may include at least one radial cam or tooth which may engage in the at least one groove. Such a groove and a cam may be easily manufactured. In addition, the coupling sleeve may thereby be quickly and easily rotationally coupled to or decoupled from the holding element.

If the coupling sleeve can be released by the holding element by a displacement relative to the holding element, engagement elements may be brought into engagement with counter-engagement elements in the coupling sleeve by the holding element during the displacement. Correspondingly, in this case, the engagement elements may also be released from the counter-engagement elements by the displacement, such that the coupling sleeve may be released by the holding element and may rotate relative to the holding element.

In an alternative embodiment, the coupling sleeve and the holding element may be held by a friction fit relative to each other, which may prevent rotation between the coupling sleeve and the holding element.

In some implementations, the guide may be configured as a groove, and the holding element may be guided in the groove in a rotationally fixed manner relative to the housing by means of a formation. For this purpose, the holding element may have, for example, a tooth, a pin or some other shape which can engage in the groove. In some implementations, the guide may include several grooves, and the holding element may accordingly include several formations.

Alternatively, the holding element may include a groove, and the housing, a housing insert, or some other element fixed to the housing may include a formation which may engage in the groove.

The holding element may include an opening in which the coupling sleeve may be received. This arrangement may save space axially since the holding element may not have to be placed on the distal or proximal side of the coupling sleeve. The holding element may be sleeve-shaped or ring-shaped, and may interact or couple via its outer side with the housing, or with any housing insert that may be present. The inner side of the opening may interact or couple with an outside of the coupling sleeve.

In some implementations, the holding element may not include an opening and, for instance, may not be rotationally symmetrical. For example, the holding element may be placed only on one side of the coupling sleeve in order to hold it relative to the housing.

In some implementations, the holding element may be disk-shaped and may include the opening in the center. The coupling sleeve may be received coaxially with the holding element in the opening. As a result, the holding element may be constructed in a compact manner.

The dose setting element may be configured as a dosing sleeve which may be held axially on the holding element, such that the holding element may move together with the dosing sleeve in the direction of the longitudinal axis.

The dosing sleeve may be connected by a threaded connection to the housing or a housing insert. In this case, the dose being dispensed may be set or corrected by means of a screwing movement. Furthermore, the coupling sleeve may be arranged coaxially in the dosing sleeve such that the dosing sleeve is arranged radially between the coupling sleeve and the housing or housing insert.

The dosing sleeve may be held in the axial direction on the holding element, for instance snapped onto it, such that the holding element may move axially together with the dosing sleeve relative to the housing for dose setting, dose correction, and dose dispensing. The dosing sleeve may, however, be rotated relative to the holding element, which may be rotationally fixed to the housing. The holding element may be arranged on a distal side of the dosing sleeve.

In some implementations, the dosing device may include an elastic element which may hold the coupling sleeve with a biasing force in a dosing position in which the coupling sleeve is held in a rotationally fixed manner relative to the holding element. Where the coupling sleeve is held in a rotationally fixed manner to the holding element by means of a toothed engagement, then engagement elements of the coupling sleeve may be in engagement with the counter-engagement elements of the holding element in the dosing position.

As a result of the biasing, the biasing force may need to first be overcome in order to move the coupling sleeve out of the dosing position. This may reduce the risk that the coupling sleeve will unintentionally move away from the dosing position and the drive device will be actuated. In the dosing position, the coupling sleeve may be prevented from rotation and thus may be prevented from unintentionally driving the drive device.

If the coupling sleeve is moved from the dosing position in the distal direction relative to the holding element against the biasing force, the coupling sleeve may be released by the holding element such that the coupling sleeve may rotate relative to the holding element and to the housing.

The elastic element may be elastically deformed, and the compression may generate the biasing force. The elastic element may, for example, be configured as a click disk, a metallic spring, an elastically deformable metal element, or an elastic plastic material, such as a rubber element.

The elastic element may include a base body and at least two elastic arms, the base body may be oriented in a plane perpendicular to the longitudinal axis of the housing, a first of the two arms may point in the proximal direction, and a second of the two arms may point in the distal direction. The arms may be attached to the base body in such a way that the arms may be compressed, deflected or bent in the axial direction. The elastic element may be compressed in its axial length by elastic deformation of the arms towards the base body. As a result, a biasing force may be generated with which the coupling sleeve can be held in the dosing position.

Furthermore, in some implementations, the base body may include an opening, such that the base body may be ring-shaped and may, for example, surround the coupling sleeve.

In addition, the dose setting element may include teeth, and the coupling sleeve may include teeth, where a first of the at least two arms may interact with the teeth of the dose setting element, or a second of the at least two arms may interact with teeth of the coupling sleeve, to generate an acoustic or tactile signal. For example, by rotating the dose setting element relative to the elastic element, the first or the second arm may slide over the teeth of the dose setting element. As a result, the arm may be elastically deflected more and more by the rising tooth flank until the arm has passed the highest point of the tooth. The arm may then spring back and generate an acoustic and/or tactile signal, such as a clicking sound, which the user may perceive. In the same way, an acoustic and/or tactile signal may be generated when an arm slides over the teeth of the coupling sleeve. In order to generate these signals clearly, the teeth of the dose setting element and the coupling sleeve may be configured in a saw tooth shape.

The teeth and the elastic element may be arranged in such a way that the first arm may be moved over the teeth of the dose setting element in a first direction of rotation, while the second arm may not, however, be moved relative to the teeth of the coupling sleeve. In a second direction opposite to the first direction of rotation, the second arm may then be moved over the teeth of the coupling sleeve, while the first arm may not be moved relative to the teeth of the dose setting element. As a result, an acoustic and/or tactile signal may be generated in both directions of rotation.

The dose setting element and the coupling sleeve may each include a flange in a proximal region, and the elastic element may be arranged between these flanges in the direction of the longitudinal axis. The elastic element may thus act on a flange surface and may therefore transfer a biasing force, e.g., a preloaded or a pretensioned force, of the elastic element to the dose setting element and the coupling sleeve. The flange surface may be oriented at right angles to the longitudinal axis, e.g., perpendicular to the longitudinal axis.

Since the elastic element may be arranged in a proximal region, the elastic element may not need to be placed in the region of the holding element, where a space-saving arrangement may otherwise not be realized.

Furthermore, in some implementations, the dosing device may include a housing insert which may include a recess which may form the guide for the holding element. The recess may be configured in the form of a groove in which the holding element may be guided in the longitudinal direction and may be held in a rotationally fixed manner relative to the housing insert. The housing insert may be arranged coaxially with the housing. The housing insert may include a cylindrical, sleeve-shaped or shell-shaped form. The housing insert may be immovable in the axial and radial directions relative to the housing, and may be fixed to the housing, for example by means of a snap connection.

According to implementations, the housing insert may be sleeve-shaped and may be placed in the interior of the housing coaxially with the longitudinal axis of the housing. Via the housing insert, the holding element may be guided independently of the housing. The housing may therefore be configured for different designs independently of the holding element and the coupling sleeve.

The housing insert may include an internal thread with which the dose setting element may be threadedly connected, such that the dose setting element may be screwed into and out of the housing insert for setting and correcting a dose. The housing insert may be made in one or more parts. For example, the housing insert may be configured as a sleeve which supports the drive device in a distal region, and may support the dose setting element in a proximal region. Alternatively, the housing insert may also include a first part which may support the drive device and a second part which may accommodate the dose setting element.

In some implementations, the drive device may include a drive sleeve and a piston rod. In this case, the drive sleeve may be mounted in the housing insert in a manner allowing rotation, but may be axially fixed, relative to the housing insert. Furthermore, the housing insert may include a second internal thread for receiving the piston rod. Where the housing insert forms the guide for the holding element and also supports the dosing sleeve and the drive device, the housing may only serve as an outer casing and may have no further function. The housing may therefore be independent of the elements and functions of the dosing device, and may accordingly be designed independently, for example in order to meet certain ergonomic or aesthetic requirements.

BRIEF DESCRIPTION OF THE DRAWINGS

Implementations are described herein in connection with the attached figures, which are intended to show the basic possibilities of the disclosed implementations and are in no way intended to be interpreted as restrictive.

FIG. 3 is a cross-sectional view of the injection apparatus of FIG. 1 in an initial position, where the cross-section runs through the longitudinal axis of the injection apparatus;

FIG. 4 is a cross-sectional view of the injection apparatus of FIG. 1 running through a plane perpendicular to the longitudinal axis of the injection apparatus;

FIG. 5 is a cross-sectional view through the longitudinal axis of the injection apparatus of FIG. 1 in a position with a set dose to be administered;

FIG. 6 is an enlargement of the cross-sectional view through the longitudinal axis of the injection apparatus of FIG. 1 in the region of the holding element, the coupling sleeve being released by the holding element in the position shown;

FIG. 7 is a cross-sectional view perpendicular to the longitudinal axis of the injection apparatus of FIG. 1, the cross-section running through the injection apparatus in the region of the holding element;

FIG. 8 is an isometric view of the coupling sleeve of the injection apparatus of FIG. 1, with the holding element and the drive sleeve;

FIG. 11 is an isometric view of the click disk of the injection apparatus of FIG. 1;

FIG. 12 shows a proximal end region of a second embodiment of the injection apparatus according to implementations of the present disclosure, the knob of the dosing sleeve being shown with a section removed to facilitate understanding;

FIG. 15 shows a proximal end region of a third embodiment of the injection apparatus according to implementations of the present disclosure, the knob of the dosing sleeve being shown with a section removed to facilitate understanding;

FIG. 16 is an isometric view of the click disk of the injection apparatus of FIG. 15;

FIG. 17 shows a proximal end region in a cross-sectional view of the injection apparatus of FIG. 15 along the longitudinal axis;

FIG. 20 is an isometric view of a further embodiment of a dosing sleeve;

FIG. 21 is an isometric view of a further embodiment of a housing insert;

FIG. 22 is an isometric view of a further embodiment of a holding element and a coupling sleeve when setting and correcting a dose;

FIG. 23 is a cross-sectional view of the holding element and the coupling sleeve of FIG. 22, the cross-section running parallel to the longitudinal axis through the ratchet arms;

FIG. 24 shows the embodiment of FIG. 22 during the dispensing of a dose; and

FIG. 25 is a cross-sectional view of the embodiment of FIG. 24 during dispensing, the cross-section running parallel to the longitudinal axis through the ratchet arms.

DETAILED DESCRIPTION

Figures 1, 2:
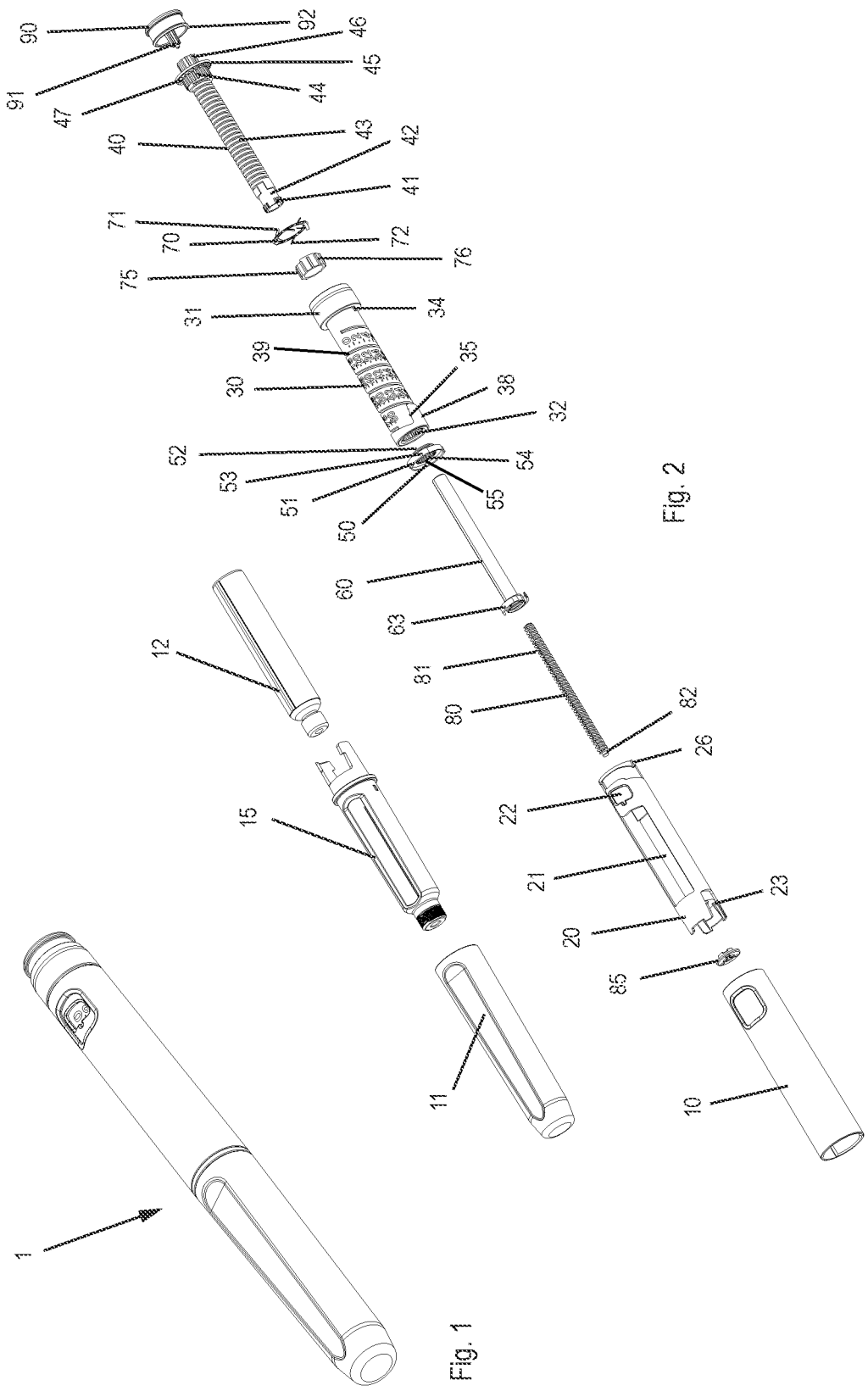
FIG. 1 is an isometric view of a first embodiment of the injection apparatus according to implementations of the present disclosure.
FIG. 2 shows an isometric, exploded view of the individual parts of the dosing device of the injection apparatus of FIG. 1.

FIG. 1 is an isometric view of an injection apparatus according to a first embodiment of the present disclosure in the form of an injector 1, which may include the dosing device according to implementations of the present disclosure. FIG. 2 shows the individual parts of the injector 1, with the dosing device in an exploded view. The distal end of the injector 1 where product dispensing occurs is situated in the left region of FIG. 2, and the proximal end of the injector 1 is situated in the right, upper region of FIG. 2.

In the embodiment shown, the injector 1 may be configured as a disposable injector. As can be seen in FIG. 2, the injector 1 may include a removable protective cap 11, an elongated, cylindrical housing 10 in which a housing insert 20 may be situated, a carpule holder 15 in which a carpule 12 with a medical substance is held, a dose setting element configured as a dosing sleeve 30 for setting a dose, a holding element 50 which may be coupled to the dosing sleeve 30, a drive sleeve 60, a coupling sleeve 40 for coupling the dosing sleeve 30 to the drive sleeve 60, and a piston rod 80 which may be driven by the drive sleeve 60 to dispense the medical substance from the carpule 12.

The structural features of the individual components of the injector 1 are discussed in detail as follows. The functions of setting, correcting and dispensing a dose are also described throughout.

The carpule holder 15 may be snapped onto the housing 10 in a rotationally fixed and axially fixed manner at a distal end of the housing 10 by means of a snap connection. The carpule holder 15 may support the carpule 12 and may have at its distal end a connecting element to which an injection needle may be attached.

The housing insert 20 may have a cylindrical shape and may be arranged coaxially in the housing 10. Via cams 26 on its outer side, which may engage in corresponding recesses on the inner side of the housing 10, the housing insert 20 may be snapped onto the housing 10 in an axially and rotationally immovable manner. In a distal region, the interior of the housing insert 20 may include a first internal thread 27 into which the piston rod 80 may be screwed, as can be seen in FIG. 3. Also in the distal region, the interior of the housing insert 20 may include a cylindrical receptacle with a circumferential bead 24, and the bead 24 may form an axial holder for the drive sleeve 60, which can be seen in FIG. 3.

In the proximal region of the housing insert 20, a second internal thread 28 may be provided, into which the dosing sleeve 30 may be screwed. In the region of this second internal thread 28 of the housing insert 20, a radial passage or an opening 22 (shown in FIG. 2) may be formed in the shell of the housing insert 20. The housing 10 may also include an opening in the radial direction at this point. As a result, a scale printed on the screwed-in dosing sleeve 30 can be read through the housing 10 and insert 20 from the outside. The housing insert 20 may thus support the piston rod 80, drive sleeve 60, and dosing sleeve 30 in a manner allowing rotation relative to the housing 10.

In an axially central region of the housing insert 20 may be provided axially elongated recesses 21 in the shell of the housing insert 20, which may be arranged offset from each other by 180° in the circumferential direction; see FIG. 2. Through these recesses 21, which may form a groove when the housing insert 20 is installed, the holding element 50 may be guided in the axial direction in the housing 10 and may be held in a rotationally fixed manner on the housing 10, as described in detail below.

Furthermore, in the distal region of the housing insert 20, the inner side may include ribs 23 which may be distributed over the circumference of the housing insert 20 and which may project radially towards the center. The ribs 23 may have a slope when viewed in the axial direction. The slope may increase in the proximal direction. In other words, the ribs 23 may be axially wedge-shaped and may have a lower radial height distally than proximally, the radial height may steadily increase in the proximal direction (i.e., slope). The ribs 23 may be dimensioned so that they may be plastically deformable. The carpule 12 may first be inserted into the carpule holder 15. The carpule holder 15 may then be connected to the housing insert 20 with a snap connection. When the carpule holder 15 is brought together with the housing insert 20, the carpule 12 situated in the carpule holder may first touch the ribs 23 of the housing insert 20 on the edge pointing towards the center. If the carpule holder 15 is pushed further in the proximal direction into the housing insert 20, the ribs 23 may deform plastically. This means that the ribs 23 may be permanently deformed by the carpule 12. The ribs 23 may either be pushed to the side as a whole from their original position, or the ribs 23 may at least partially take on the shape of the outer contour of the carpule 12. When the carpule holder 15 is then snapped onto the housing 10, the carpule 12 may be held axially and radially immovably in the carpule holder 15, since the carpule holder 15 may exert a clamping force in the proximal direction on the carpule 12 and may thereby press the carpule 12 against the deformed ribs 23.

As mentioned, the dosing sleeve 30 may be threadedly connected to the housing insert 20. For this purpose, the dosing sleeve 30 may include a helical groove on its outer side which may form an external thread 39 which may engage with the internal thread 28 in the housing insert 20. The dosing sleeve 30 may have the shape of a hollow cylinder or a sleeve and, at the proximal end, may include a region with a diameter which is greater than the remaining region of the dosing sleeve 30, and which may serve as a handle or knob 31. This knob 31 may not fit into the housing 10; rather, as can be seen in FIG. 3, the knob 31 may rest on the proximal end of the housing 10. At the proximal end of the region with the smaller diameter, the dosing sleeve 30 may include an axially oriented web 34 on the outer side thereof, which can be seen in FIG. 2. In the fully screwed-in position of the dosing sleeve 30, the web 34 may strike a radially shaped stop in the housing insert 20, such that the minimum dose and/or the screwing movement of the dosing sleeve 30 into the housing may be limited by the web 34.

At its distal end, the outer side of the dosing sleeve 30 may also protrude, such that a shoulder 35 is defined on the outer side. Alternatively, a stop sleeve 38 may also be pushed onto the dosing sleeve 30 at the distal end of the dosing sleeve 30, and may be connected to it in a rotationally fixed and axially fixed manner, as can be seen in FIG. 2. In this case, one edge of the stop sleeve 38 may form the shoulder 35. This may serve as the maximum stop. When the dosing sleeve 30 is screwed out of the housing 10 to the maximum extent, the shoulder 35 may come into contact with a stop in the housing insert 20. This may limit the unscrewing of the dosing sleeve 30 from the housing 10, such that no more than the maximum dose that can be dispensed may be set. In an alternative embodiment, the dosing sleeve 30 may also include an axially aligned web in the distal region, which may strike a stop in the housing insert 20 in the end position.

In the region of the smaller diameter of the dosing sleeve 30, axial grooves 32 may be formed on the inner side of the hollow cylinder of the dosing sleeve 30, in which a stop nut 75 may be guided axially and in a rotationally fixed manner. For this purpose, the stop nut 75 may include axial webs 76 on its outer circumference, which may protrude into the grooves 32. At its distal end, the dosing sleeve 30 may include on the inner side thereof a circumferential collar 33 projecting radially towards the center, which can be seen in FIG. 3. A cylindrical region of the holding element 50 with a circumferential groove 51 may be snapped into place above this circumferential collar 33. The holding element 50 may thereby connected to the dosing sleeve 30 in a rotationally free but axially fixed manner.

The holding element 50 may be disk-shaped and, as can be seen in FIG. 2, when looking in the axial direction, has a first distal portion 51 with a greater outer diameter, and a second proximal portion 52 with a smaller outer diameter, which may be inserted into the dosing sleeve 30. The holding element 50 may be snapped via the proximal portion 52 onto the dosing sleeve 30, as described herein. On the outer side of the distal portion 51, two radial formations or cams 53 may be formed, which may extend in sections in the circumferential direction and may be arranged offset from each other by 180°. These cams 53 may be received in the elongated recesses 21 in the housing insert 20, and may be guided by the recesses 21 in the axial direction. As a result, the holding element 50 may be guided axially and may be rotationally fixed relative to the housing insert 20 and to the housing 10. Furthermore, the holding element 50 may include a continuous axial opening 55 in its center, e.g., may be ring-shaped. A plurality of axial grooves 54 may be distributed over an internal circumference of the opening 55. Teeth 41 distributed over the external circumference and arranged in the distal end region of the coupling sleeve 40 may engage in these grooves 54 of the holding element 50, for example, as can be seen in FIG. 7.

The cylindrical, elongated coupling sleeve 40 may protrude on the proximal side of the teeth 41, and may include a flat cylindrical portion 42 (FIGS. 2 and 8), the outside diameter of which may be smaller than the innermost inside diameter of the holding element 50, such that the holding element 50 may not contact the cylindrical portion 42 when the holding element 50 is positioned in the axial direction over this section 42. The external thread 43 of the coupling sleeve 40 may begin on the proximal side of the cylindrical portion 42 and may extend as far as a proximal end region of the coupling sleeve 40. The stop nut 75 may be in threaded engagement with the external thread 43. As can be seen in FIG. 2, the proximal end of the coupling sleeve 40 may include a flange 45, and a hollow cylindrical end portion 46 may have a smaller diameter than the other portions of the coupling sleeve 40. The flange 45 may be disk-shaped or shield-shaped and may adjoin a cylindrical portion which may have a greater diameter than the external thread 43. This portion, which may be situated on the distal side of the flange 45, may have connecting webs 44 arranged around the circumference which may be inserted into the grooves 32 in the dosing sleeve 30, such that the coupling sleeve 40 may be coupled to the dosing sleeve 30 in a rotationally fixed manner. The disk-shaped flange 45 may include saw teeth 47 arranged in the circumferential direction on a distal flange surface which may be arranged perpendicular to the longitudinal axis of the injector 1; see FIG. 2.

If the coupling sleeve 40 is inserted into the dosing sleeve 30, for instance as shown in the starting position in FIG. 3, there may be an interior space defined between the disk-shaped flange 45 of the coupling sleeve 40 and a terminal wall or a flange of the dosing sleeve 30, which also has saw teeth 36 on an end face of this portion of the dosing sleeve 30. The interior space may be somewhat longer in the axial direction than the connecting webs 44 on the coupling sleeve 40, such that in a dosing position of the coupling sleeve 40 the connecting webs 44 do not engage in the grooves 32 of the dosing sleeve 30, as a result of which the coupling sleeve 40 may be free to rotate with respect to the dosing sleeve 30.

Figure 10:
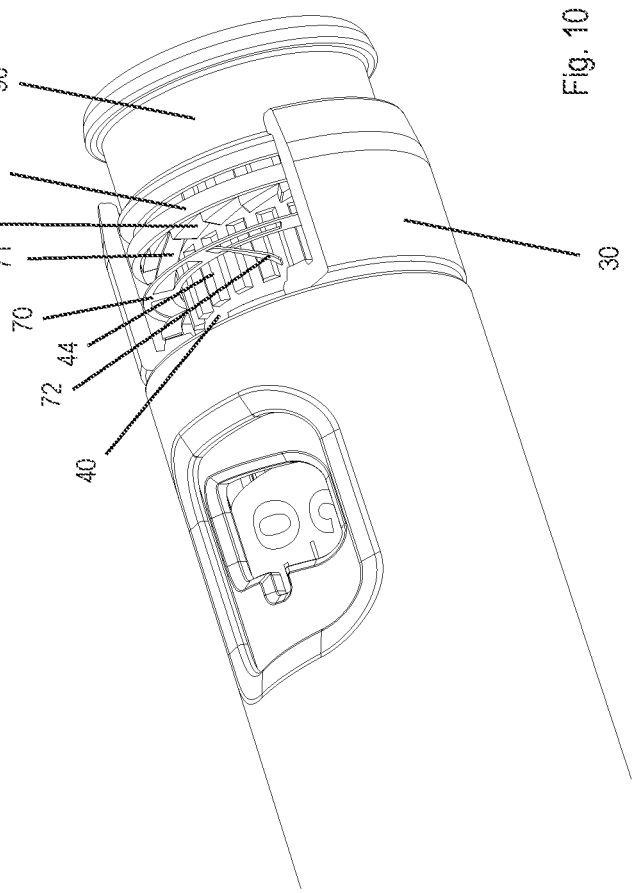
FIG. 10 is an isometric view of the proximal end region of the injection apparatus of FIG. 1, the knob of the dosing sleeve being shown with a section removed to facilitate understanding.

The click disk 70, which may serve as an elastic element, can be seen in FIGS. 10 and 11. In contrast to the other components of the injector 1, which may be made of plastic, the click disk 70 may be made of sheet metal. As can best be seen in FIG. 11, the click disk 70 may be circular and has an opening in the middle, such that the click disk 70 has the shape of a ring. This ring shape of the click disk 70 may include punched-out distal and proximal arms 71, 72. This means that the arms 71, 72 may be formed of the material of the ring, may be connected to the ring on one end, and may have a free end which protrudes from the ring, such that the arms 71, 72 may each form a resilient and elastic element. The click disk 70 may include four arms 71, 72 on each side—four distal arms 72 protruding from the ring in the distal direction and four proximal arms 71 protruding in the proximal direction.

The distal arms 72 of the click disk 70 may interact with or slide over the saw teeth 36 of the dosing sleeve 30, while the proximal arms 71 of the click disk 70 may interact with or slide over the saw teeth 47 of the coupling sleeve 40; see FIG. 10.

As mentioned, the click disk 70 may be arranged axially between the dosing sleeve 30 and the coupling sleeve 40. The resilient and elastic arms 71, 72 may be slightly biased or tensed. Due to the arms 71, 72 protruding from the click disk 70, the dosing sleeve 30 and the click disk 70 may be axially pushed apart and pressed against a stop which may be formed by a release button 90 and which may determine a maximum axial distance between the dosing sleeve 30 and the coupling sleeve 40.

In FIGS. 2 and 3, the release button 90 can be seen, which may be situated at a proximal end of the injector 1. The release button 90 may include an outer hollow cylinder, which may be closed-off by a proximal wall, and an axial pin-shaped formation 91 placed in the center of the outer hollow cylinder. The release button 90 may be situated in the hollow cylindrical end portion 46 of the coupling sleeve 40. The release button 90 may be supported on the coupling sleeve 40 by a distal tip of the axial pin-shaped formation 91, such that the release button 90 may be rotated relative to the coupling sleeve 40. The outer hollow cylinder of the release button 90, on the other hand, may be axially connected to the dosing sleeve 30, for instance where a circumferential collar 92 of the release button 90 engages over a circumferential bead 37 on the proximal end of the dosing sleeve 30, as shown in FIG. 3. As a result, the release button 90 may be prevented from moving axially away from the dosing sleeve 30 in the proximal direction. The release button 90 may, however, be held in a manner allowing rotation relative to the dosing sleeve 30 and to the coupling sleeve 40.

As mentioned, a stop nut 75 may be screwed onto the external thread 43 of the coupling sleeve 40. The stop nut 75 may include axially aligned webs 76 on an outer side which may engage in the axial grooves 32 on the inner side of the dosing sleeve 30. The stop nut 75 may accordingly be rotatable relative to the coupling sleeve 40, and may be axially displaceable, but non-rotatable, relative to the dosing sleeve 30.

The drive sleeve 60 may be inserted into the hollow cylinder of the coupling sleeve 40. As can be seen in FIG. 4, the coupling sleeve 40 may include in its axial passage, over the entire axial length, two axial shoulders or webs 48 offset in the circumferential direction, which may have the cross-sectional shape of a wedge. These webs 48 may be received in correspondingly shaped axial grooves 61 on the outer side of the drive sleeve 60, such that the drive sleeve 60 may be mounted in the coupling sleeve 40 in a rotationally fixed manner, but may be axially displaceable relative to the coupling sleeve 40. The webs 48 may be arranged in such a way that in the direction of rotation for dispensing, the steep or radial flank of the wedge-shaped web 48 rests against the correspondingly shaped radial flank of the groove 61, such that in the direction of rotation for dispensing, a torque may be transferred from the coupling sleeve 40 to the drive sleeve 60.

At its distal end, the drive sleeve 60 may include a section with a greater diameter which, as mentioned herein, may include a circumferential groove 62 in an interior, which may be snapped onto a circumferential bead 24 of the housing insert 20, such that the drive sleeve 60 may be held axially relative to the housing insert 20 and thus to the housing 10, but may be rotatably mounted relative to the housing insert 20 and the housing 10, as shown in FIG. 3. In addition, the drive sleeve 60 may include two radially protruding, flexible ratchet arms 63 in this distal portion, which may be clearly seen in FIG. 8. The ratchet arms 63 may cooperate with saw teeth 25, which may be arranged along the circumference of an axial passage in the housing insert 20 (FIG. 3). As a result, the drive sleeve 60 may only be rotated in one direction in which the ratchet arms 63 may slide over the flat flanks of the saw teeth 25. In the opposite direction, the ratchet arms 63 may strike against steep or radial flanks of the saw teeth 25, and may thereby prevent a rotation of the drive sleeve 60 relative to the housing insert 20 and thus relative to the housing 10.

Furthermore, the drive sleeve 60 may include a centrally arranged circular opening over its entire axial length, and axially aligned webs or grooves 61 offset by 180° may be situated in the circumferential direction, which may be wedge-shaped in cross-section, like the webs 48 in the interior of the coupling sleeve 40, for instance as shown in FIG. 4.

In FIG. 4, it can also be seen that the piston rod 80 may include formations over its axial length which may form a shoulder 81. The piston rod 80 thus may have a cross-section which fits positively into the opening of the drive sleeve 60, such that the piston rod 80 may be mounted in a rotationally fixed but axially displaceable manner relative to the drive sleeve 60. At the distal end of the piston rod 80 a button-shaped end or termination 82 of the piston rod 80 may be provided (FIG. 2), which may enable a snap connection with a flange 85, such that the flange 85 may be rotatable relative to the piston rod 80, but may be held immovable in the axial direction on the piston rod 80. The flange 85 may act on a stopper 13 (FIG. 3) in the carpule 12 in order to dispense the medical substance from the carpule 12.

In FIG. 3, the injector 1 is shown in an initial position. To set a dose, the dosing sleeve 30 may be rotated by its knob 31 relative to the housing 10. Since it is in threaded engagement with the housing insert 20, the dosing sleeve 30 is accordingly screwed out of the housing insert 20. The number scale printed on the dosing sleeve 30 (FIG. 2) may be seen through the openings 22 in the housing insert 20 and in the housing 10, and may help to set the desired dose. The screwing movement of the dosing sleeve 30 may rotate the dosing sleeve 30 relative to the click disk 70. As a result, the distal arms 72 of the click disk 70 may slide over the flat flanks of the saw teeth 36 of the dosing sleeve 30, and may generate a clicking sound in the process. The click disk 70 and the coupling sleeve 40 may not be rotated. However, when the dosing sleeve 30 is unscrewed from the housing insert 20, the click disk 70 and the coupling sleeve 40 may be axially entrained and thus may be axially moved out of the housing insert 20 (and the housing 10). The coupling sleeve 40 may be held with the holding element 50 in a rotationally fixed manner relative to the housing insert 20 and relative to the housing 10 via the toothed engagement, since the holding element 50 is in turn held in a rotationally fixed manner on the housing insert 20 and thus on the housing 10. The injector 1 with a set dose is shown in FIG. 5.

If too high a dose is accidentally set, the dose may be corrected by screwing the dosing sleeve 30 back into the housing insert 20. The coupling sleeve 40 may also be held in a rotationally fixed manner relative to the housing insert 20 by means of the holding element 50. During the reverse rotation, the distal arms 72 and thus the entire click disk 70 may be rotated via the steep flanks of the saw teeth 36 in the dosing sleeve 30. This may have the consequence that the proximal arm 71 of the click disk 70 may be guided over the flat flank of the saw teeth 47 of the coupling sleeve 40, as a result of which the proximal arms 71 may generate a clicking sound and a tactile signal. As such, either the distal arms 72 (increasing the dose) or the proximal arms 71 (reducing the dose) may generate a clicking sound and a tactile signal.

Since the elastic arms 71, 72 of the click disk 70 may be slightly compressed in the axial direction, a biasing force may be exerted against the coupling sleeve 40, which may be held in the proximal dosing position or may be pressed in the proximal direction against a stop formed by the release button 90. The coupling sleeve 40 may thus be held by the biasing force in the dosing position in which the coupling sleeve 40 may be coupled to the holding element 50, e.g., because the teeth 41 at the distal end of the coupling sleeve 40 may engage in the grooves 54 in the holding element 50. Since the holding element 50 may be held in a rotationally fixed manner on the housing insert 20 and housing 10, the coupling sleeve 40 may also be held in a rotationally fixed manner relative to the housing insert 20 in this position. Consequently, when setting and correcting a dose, if the dosing sleeve 30 is rotated forwards or backwards, the coupling sleeve 40 may be prevented from rotating.

Since the holding element 50 may be fixedly attached to the dosing sleeve 30 in the axial direction, the holding element 50 may be displaced axially in the proximal direction together with the dosing sleeve 30 when a dose is set. As a result, the coupling sleeve 40 may remain in the coupled position with the holding element 50, for instance even if the coupling sleeve 40 and holding element 50 are axially displaced together relative to the housing insert 20 and housing 10. With the engagement of the coupling sleeve 40 in the holding element 50 (see also FIG. 7) and the resulting rotational coupling of the coupling sleeve 40 to the housing 10, an efficient anti-rotation lock may be provided.

The same applies when correcting a set dose, that is to say when the dosing sleeve 30 is screwed back into the housing insert 20. In this case, the dosing sleeve 30 may push the coupling sleeve 40 axially in the distal direction back into the housing insert 20 via the release button 90 fixed axially to the dosing sleeve 30. Since the coupling sleeve 40 may be held in position by the biasing force of the click disk 70 relative to the holding element 50 and may thus remain in engagement therewith, the coupling sleeve 40 may be prevented from rotating relative to the housing insert 20 even when the dosing sleeve 30 is rotated back in the distal direction.

During the setting and correction of the dose, i.e., when unscrewing the dosing sleeve 30 from the housing insert 20 as well as when screwing the dosing sleeve 30 into the housing insert 20, the connecting webs 44 of the coupling sleeve 40 may not engage in the grooves 32 in the interior of the dosing sleeve 30, which may result in the dosing sleeve 30 and coupling sleeve 40 being rotated relative to each other, e.g., as shown in FIGS. 3 and 5.

Since the coupling sleeve 40 may be prevented from rotating when setting the dose and when correcting a dose, the drive sleeve 60 may also not be rotated and the piston rod 80 may not be driven. This may thus prevent unwanted dispensing.

The stop nut 75 may be guided axially and in a rotationally fixed manner in the dosing sleeve 30. When the dosing sleeve 30 is rotated, the stop nut 75 may be rotated together with the dosing sleeve 30, as a result of which the stop nut 75 may be screwed in the proximal direction on the external thread 43 of the coupling sleeve 40. When correcting/turning back the dosing sleeve 30, the stop nut 75 may accordingly be screwed back in the distal direction.

In order to dispense a set dose, the user may press the release button 90 in the distal direction. The release button 90 may slide in the distal direction relative to the dosing sleeve 30, due to the pressure force, together with the coupling sleeve 40. The flexible arms 71, 72 may be compressed axially by the front surface of the flange 45 of the coupling sleeve 40 and by the front surface of the dosing sleeve 30. Since the distal movement of the release button 90 may also move the coupling sleeve 40 distally relative to the dosing sleeve 30, the connecting webs 44 on the coupling sleeve 40 may be inserted into the grooves 32 in the dosing sleeve 30, such that the coupling sleeve 40 may be rotationally coupled to the dosing sleeve 30. At the same time, during this distal displacement of the coupling sleeve 40, the teeth 41 at the distal end of the coupling sleeve 40 may be pushed out of the grooves 54 in the holding element 50, such that the grooves 54 lie above the cylindrical portion 42 of the coupling sleeve 40 and there may no longer be any engagement, as shown in FIG. 6. As a result, the coupling sleeve 40 may no longer be rotationally coupled to the holding element 50 and thus to the housing insert 20, and the coupling sleeve 40 may rotate relative to the housing insert 20 and relative to the housing 10.

In a further embodiment, the rotation of the coupling sleeve 40 may first be released by the holding element 50 (by sliding the teeth 41 of the coupling sleeve 40 out of the grooves 54 of the holding element 50), and only then, when the coupling sleeve 40 is no longer held by the holding element 50, may the coupling sleeve 40 be rotationally coupled to the dosing sleeve 30. In a further embodiment, however, the coupling sleeve 40 may first be rotationally coupled to the dosing sleeve 30, and only after this coupling may the coupling sleeve 40 be rotationally released by the holding element 50.

If the coupling sleeve 40 is displaced further in the distal direction relative to the dosing sleeve 30, the pressure force of the user may be transmitted from the flange 45 of the coupling sleeve 40 in the distal direction via the click disk 70 to the end-face surface of the dosing sleeve 30. Since the dosing sleeve 30 may be screwed into the housing insert 20 via the external thread 39 of the dosing sleeve 30 (FIG. 2), the dosing sleeve 30 may begin to screw into the housing insert 20 with a screwing movement under the distal compressive force.

Since the coupling sleeve 40 may now be rotationally coupled to the dosing sleeve 30 and may no longer be held in a rotationally fixed manner via the holding element 50, the coupling sleeve 40 may also be rotated relative to the housing insert 20 and the housing 10 by the rotating dosing sleeve 30. As a result, the drive sleeve 60, which may be rotationally connected to the coupling sleeve 40, may also be rotated. The drive sleeve 60 may be held axially on the housing insert 20 and therefore may not move axially relative to the housing 10 during rotation. The rotation of the drive sleeve 60 may drive the piston rod 80, which may be rotationally coupled to the drive sleeve 60 and which may thereby result in the piston rod 80 screwing into the internal thread 27 of the housing insert 20 in the distal direction. As a result, the flange 85 at the distal end of the piston rod 80 may be displaced axially relative to the housing 10, and may thus displace the stopper 13 situated in the carpule 12 in the distal direction relative to the carpule 12. As a result, the medicinal substance may be released from the cartridge for dispensing.

Figure 9:
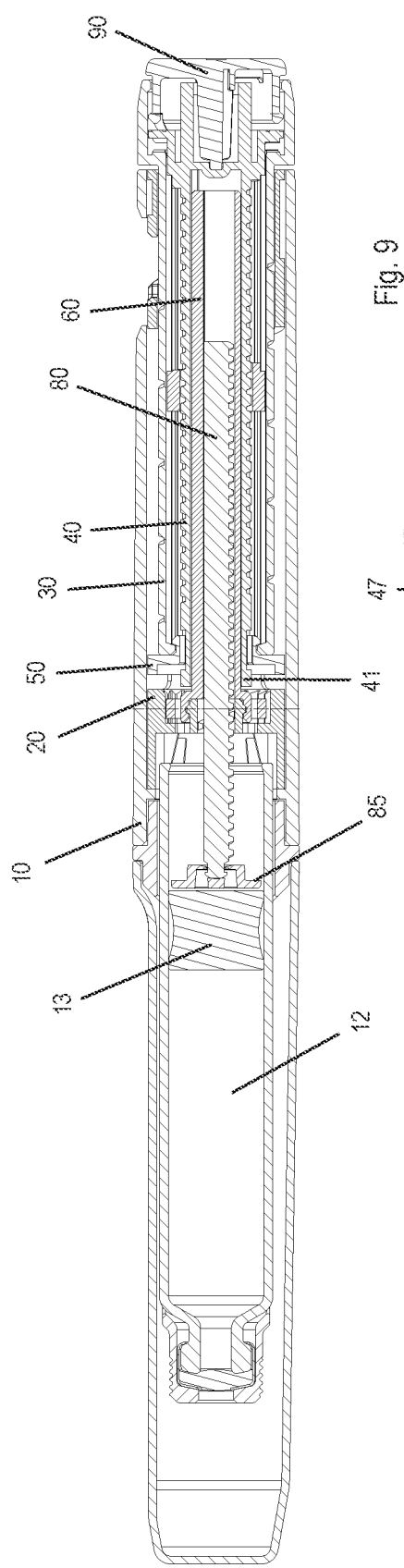
FIG. 9 is a cross-sectional view through the longitudinal axis of the injection apparatus of FIG. 1 after a dose has been dispensed.

The flexible ratchet arms 63 of the drive sleeve 60 may be moved during the rotation of the drive sleeve 60 over the flat flanks of the saw teeth 25 of the housing insert 20, as a result of which a clicking sound and a tactile signal may be generated. Due to the saw tooth shape, the ratchet arms 63 may only be guided over the saw teeth 25 in the dispensing direction. In the opposite direction, the ratchet arms 63 may lie against the radial flanks of the saw teeth 25, and may thus prevent rotation of the drive sleeve 60. As a result, the piston rod 80 may only be moved in the dispensing direction. The position of the injector 1 in which the set dose is dispensed is shown in FIG. 9.

As mentioned, when the dose is dispensed, the rotary coupling does not result in any relative movement between the coupling sleeve 40 and the dosing sleeve 30. As a result, the stop nut 75 may also be rotated, but the stop nut 75 may not be displaced relative to the coupling sleeve 40. This means that the stop nut 75 may not be moved on the external thread 43 in the distal or proximal direction. Thus, the stop nut 75 may only be moved relative to the coupling sleeve 40 and relative to the dosing sleeve 30 during dose setting or dose correction. The thread pitch and the dimension of the stop nut 75 may be selected in such a manner that the stop nut 75 strikes a radial stop on the coupling sleeve 40 at the proximal end of the external thread 43 of the coupling sleeve 40 when the maximum dispensable dose has been set. This may ensure that the user may set and dispense a dose several times, but that a dose which exceeds the capacity of the carpule 12 cannot be set.

Figure 14:
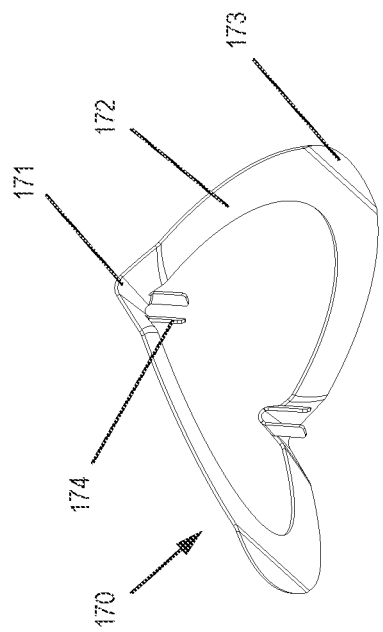
FIG. 14 is an isometric view of the click disk of FIG. 13.
Figure 13:
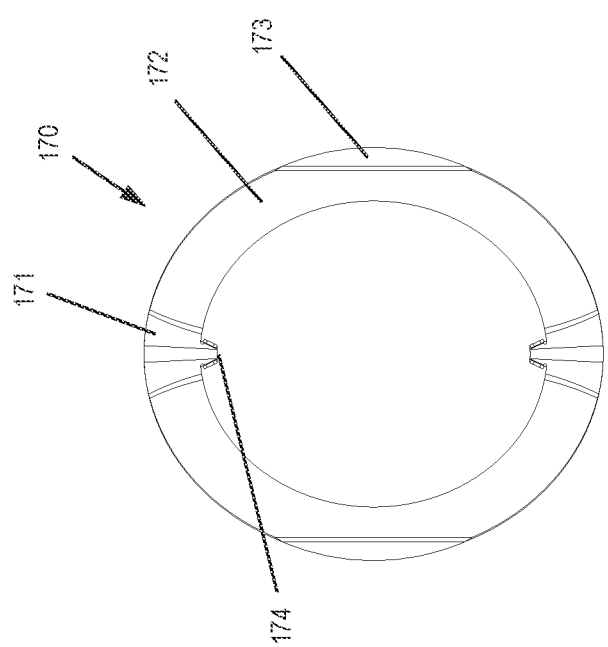
FIG. 13 is a top view of the click disk of the injection apparatus of FIG. 12.

The injector 1 according to implementations of the present disclosure may also have alternative configurations from those described in the first embodiment of FIGS. 1 to 11. In FIGS. 12 to 14, a proximal region of an injector according to a second embodiment of the present disclosure is shown, in which the injector may include another click disk 170. In FIG. 12, part of the dosing sleeve 130 is not shown to illustrate the interior space of the dosing sleeve 130 with the click disk 170 arranged therein. The click disk 170 may be made of metal and may include a passage or opening in the center, such that the click disk 170 may define a ring. However, in the case of the click disk 170 according to FIG. 12 to 14, in contrast to the first embodiment, two halves 172 may be at an angle of approximately 30° to an installation plane which may be perpendicular to the longitudinal axis of the housing 10. On their outermost side, the two halves 172 may each have an angled section 173 which may be parallel to the installation plane, as can be seen in FIG. 14. In addition, the two inclined halves 172 may converge to form a point 171 which may have a counter-shape to the end-face teeth 131 of the dosing sleeve 130; see FIG. 12. The click disk 170 may be held by two pairs of tabs 174 projecting axially from the ring, the two pairs may be offset by 180° in the circumferential direction and may be arranged in the region of the tip 171 of the ring. The tabs 174 may engage in axial grooves in the coupling sleeve 140, as a result of which the click disk 170 may be held in a rotationally fixed manner relative to the coupling sleeve 140.

With the angled sections 173, the click disk 170 may be supported on a proximal flange 141 of the coupling sleeve 140 (FIG. 12). The elastic click disk 170 may be slightly compressed in the installed state and may thereby generate a biasing force with which the click disk 170 may hold the coupling sleeve 140 in the distal direction in the dosing position. As mentioned, in the second embodiment, the dosing sleeve 130 may include end-face teeth 131 arranged over the entire circumference at its proximal end at a terminal end face, and the end-face teeth 131 may be connected to each other with a rounded transition.

When a dose is set and corrected, the tip 171 of the click disk 170 may be moved over the end-face teeth 131 and may thereby generate a click sound and a tactile signal. Since the end-face teeth 131 may be designed symmetrically and may be connected to each other by means of a round transition, the tip 171 may be moved in both directions of rotation (e.g., for dose setting and correcting) via the end-face teeth 131. The click disk 170 may be held in a rotationally fixed manner relative to the coupling sleeve 140 in both directions of rotation by means of the tabs 174 engaging in the coupling sleeve 140. During the dispensing of the dose, when the coupling sleeve 140 is displaced in the distal direction relative to the dosing sleeve 130, the click disk 170 may be axially compressed, such that the two angled halves 172 may be pressed towards the installation plane. The coupling of the coupling sleeve 140 to the dosing sleeve 130 during dispensing takes place as described herein in connection with the first embodiment.

In FIGS. 15 to 17, a proximal region of an injector according to a third embodiment of the present disclosure is shown, which may include a click disk 270. In FIG. 15, part of the knob 231 of the dosing sleeve 230 is not shown to illustrate the interior space of the dosing sleeve 230 with the click disk 270 arranged therein. In this embodiment, in addition to the click disk 270, the injector may also include a click sleeve 250 which may include a flange on a distal side and a cylindrical portion adjoining the flange on a proximal side (FIG. 17).

As described in the first embodiment, the dosing sleeve 230 may include saw teeth 231 on an end face. In contrast to the first embodiment, the click disk 270 may be made of plastic and may include saw teeth 271, 272 on both the distal and the proximal sides, as can be seen in FIG. 16. The distal saw teeth 272 may interact with, e.g., slide over, the saw teeth 231 of the dosing sleeve 230. The click sleeve 250 may include saw teeth 251 on the distal end face of its flange, which may interact with, e.g., slide over, the proximal saw teeth 271 of the click disk 270.

As can be seen in FIG. 17, in this third embodiment the injector may include a button insert 220 which may include a hollow cylindrical portion and a disk-shaped section at the proximal end. The hollow cylindrical portion may be situated in the proximal end element 246 of the coupling sleeve 240, and the disk-shaped section may adjoin the proximal end of the coupling sleeve 240. A pointed distal end of the button insert 220 may be supported on the coupling sleeve 240. The hollow cylindrical portion of the button insert 220 may include a circumferential formation which may be received in a recess in the proximal end element 246 of the coupling sleeve 240. The button insert 220 may thereby be snapped to the coupling sleeve 240 in an axially fixed manner. As in the first embodiment, the release button 290 may include a distal formation which may be rotatably supported on the distal base in the hollow cylindrical portion of the button insert 220. In addition, the release button 290 may be snapped onto the dosing sleeve 230, as in the first embodiment. The release button 290 may be rotated relative to the button insert 220 and relative to the dosing sleeve 230.

A click spring 280 may be installed coaxially between the flange of the click sleeve 250 and the disk-shaped section of the button insert 220, as can be seen in FIG. 17. The click spring 280 may therefore be supported with its proximal end on the button insert 220 and with its distal end on the click disk 270. The click spring 280 may be compressed in the installed state, as a result of which a biasing force may be generated which may act in the distal direction on the click sleeve 250, and may press the saw teeth 251 of the click sleeve 250 against the saw teeth 271 of the click disk 270. The click disk 270, in turn, may be pressed with its distal saw teeth 272 against the saw teeth 231 of the dosing sleeve 230 by this biasing force.

During dose setting, when the dosing sleeve 230 is rotated out of the housing, there may be a relative movement of the dosing sleeve 230 and the click disk 270, and the saw teeth 231 of the dosing sleeve 230 may slide with their flat flanks over the flat flanks of the distal saw teeth 272 of the click disk 270, and may thereby generate a clicking sound and a tactile signal. The proximal saw teeth 271 of the click disk 270, however, may strike with their steep flanks against the steep flanks of the saw teeth 251 of the click sleeve 250, such that a relative movement between the click disk 270 and click sleeve 250 is prevented.

If a set dose is corrected by screwing the dosing sleeve 230 back into the housing insert, the saw teeth 231 of the dosing sleeve 230 and those of the click disk 270 may interlock in such a way that a relative movement may be prevented. However, in this case the click disk 270 may rotate together with the dosing sleeve 230 relative to the click sleeve 250, since the flat flanks of the proximal saw teeth 271 of the click disk 270 may slide over the flat flanks of the click sleeve 250, and thus may also generate a click sound and a tactile signal. The click spring 280 may ensure that the saw teeth 231 of the dosing sleeve 230, the click disk 270 and the click sleeve 250 may constantly be pressed against each other, and the clicking noise may be generated when the saw teeth move relative to each other.

When a dose is dispensed, as described in the first embodiment, the release button 290 may be displaced together with the coupling sleeve 240 relative to the dosing sleeve 230 in the distal direction against the biasing force of the click spring 280. Since the release button 290 may be axially supported on the button insert 220, which may rest against the coupling sleeve 240, the button insert 220 may also be displaced. During dispensing, the dosing sleeve 230, the coupling sleeve 240 coupled to the dosing sleeve 230, and also the click disk 270, the click sleeve 250, the click spring 280 and the button insert 220 may rotate relative to the housing and relative to the release button 290. The button insert may 220 thus prevent an element in contact with the click spring 280 from rotating relative to the click spring 280, which may otherwise result in increased friction.

Figure 19:
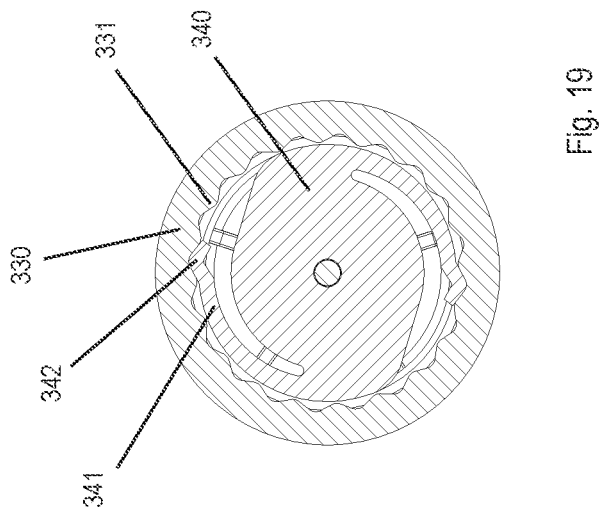
FIG. 19 is a cross-sectional view of the drive sleeve of FIG. 18 together with the dosing sleeve, with the cross-section running perpendicular to the longitudinal axis.
Figure 18:
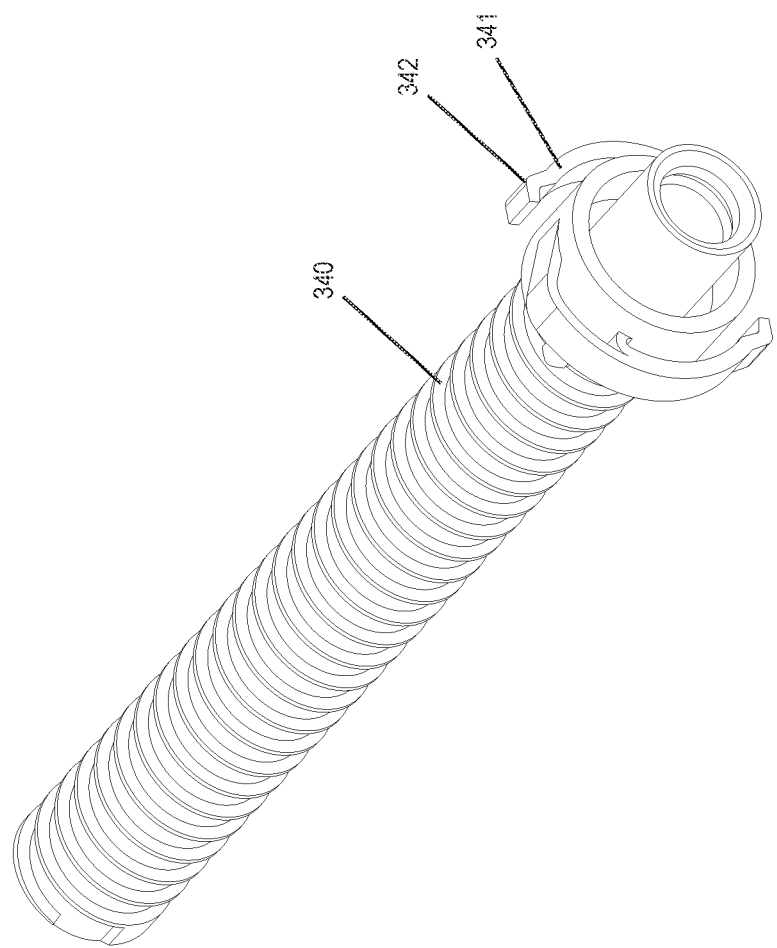
FIG. 18 shows an isometric view of a further embodiment of a drive sleeve.

FIGS. 18 and 19 show a fourth embodiment; FIG. 18 shows an isometric view of the coupling sleeve 340, and FIG. 19 shows a cutaway view perpendicular to the longitudinal axis, through the coupling sleeve 340 and the dosing sleeve 330, in the region of the radial arms 341. In this fourth embodiment, the injector may not include a click disk. Instead, the two radial, elastic arms 341 may be formed directly on the coupling sleeve 340. The arms 341 may be attached to the coupling sleeve 340 in a proximal region, and may include a radial outward extension 342 at the protruding end of the arms 341.

As can be seen in FIG. 19, the dosing sleeve 330 in this embodiment may include radial teeth 331 on an inner side, with which the radial outward extensions 342 of the arms 341 can interact, e.g., slide over. The teeth 331 may be arranged next to each other in the circumferential direction, and may be connected to each other by means of a rounded transition. As a result, the arms 341 with the outward extensions 342 may be moved in both directions of rotation (setting and correcting a dose) over the individual teeth 331 and spaces. Since the arms 341 may be elastic and may be pressed against the teeth 331 with a biasing force, a clicking sound and a tactile signal may be generated each time.

FIG. 20 is an isometric view of a variant of the dosing sleeve 430. In contrast to the first embodiment, in this variant, instead of a radial web which limits the unscrewing of the dosing sleeve 430 from the housing, an elastic element in the form of a flexible tab or a flexible arm 431 may be provided. If the dosing sleeve 430 is screwed out of the housing to the maximum extent, the protruding, flexible arm 431 may strike a stop in the housing insert.

In addition, the drive sleeve may also be designed differently than described in the first embodiment. For example, for the axial retention of the drive sleeve relative to the housing insert, the drive sleeve may be axially fixed to other elements, rather than having a snap connection. In a variant, the housing may include a wall or rib pointing radially towards the center of the housing, which may surround at least part of the distal region of the drive sleeve, such that the drive sleeve may be prevented from being displaced in the proximal direction. A stop or a wall of the housing insert may prevent displacement of the drive sleeve in the distal direction. As such, the drive sleeve may be axially immovable, but may still be rotatably mounted relative to the housing insert and the housing.

Furthermore, the injector according to implementations of the present disclosure may include a housing insert which is designed differently than described in the first embodiment. FIG. 21 shows a variant in which the housing insert may be constructed in several parts, and may include a distal housing insert 520 and a proximal housing insert 529. The distal housing insert 520 may include ribs 523 projecting radially towards the center, and may be configured for receiving the carpule 12. In addition, the distal housing insert 520 may include an internal thread 527 into which the piston rod (e.g., piston rod 80) may be screwed. Saw teeth 525 may be arranged along the circumference of an axial passage in the housing insert 520 and may cooperate for example with ratchet arms 63 of the drive sleeve 60 to permit one-way rotation of the drive sleeve 60 as described herein. The proximal housing insert 529 may include an internal thread into which the dosing sleeve can be screwed and an opening 522 in the radial direction through which the scale of the dosing sleeve may be viewed from the outside of the injection device. The proximal housing insert 529 may further include an internal radial web, which may serve as a stop in order to limit the unscrewing of the dosing sleeve. The distal and the proximal housing insert 520, 529 may each be snapped into place in the interior of the housing for instance by means of a snap connection, such that the housing inserts 520, 529 may be held axially and rotationally on the housing. Since in this embodiment, the two-part housing insert 520, 529 may not form a groove as a guide for the holding element, the groove may be provided directly in the inner wall of the housing of the injection device.

In a further embodiment, the holding element 650 and the coupling sleeve 640 may be designed differently than described previously herein. In this embodiment, the holding element 650 may include two radial ratchet arms 652 at the distal end, each of which may include a cam 653 on its end. The ratchet arms 652 may be attached to the cylindrical base body of the holding element 650 by means of a radial wall or web 651. This embodiment is shown schematically in FIG. 22-25. Only the distal end region of the coupling sleeve 640 is shown. In contrast to the embodiment described herein, the coupling sleeve 640 may include a circumferential collar 642 at the distal end. In addition, the coupling sleeve 640 may include two radial openings 641 in its cylinder, through which the radial webs 651 of the holding element 650 may protrude, such that the ratchet arms 652 are located outside a surface of the coupling sleeve 640. The drive sleeve, which is not shown in FIG. 22-25, may be situated inside the coupling sleeve 640. In contrast to the design described previously, the drive sleeve may not include any ratchet arms. The housing may include on its inner side, in the longitudinal direction, a plurality of axial grooves distributed over the circumference, in which the cams 653 may engage.

When a dose is set and corrected, the ratchet arms 652 may rest on the collar 642 of the coupling sleeve 640, as can be seen in FIGS. 22 and 23. The ratchet arms 652 may be blocked by the collar 642 and may be prevented from moving in a radial direction. The cams 653 of the ratchet arms 652 may be guided in the grooves of the housing. As a result, the coupling sleeve 640 may be prevented from rotating relative to the housing during the setting and correction of the dose, but the coupling sleeve 640 may move axially together with the holding element 650. During dispensing, the coupling sleeve 640, as described in the first exemplary embodiment, may be displaced in the distal direction relative to the dosing sleeve. As a result, the collar 642 of the coupling sleeve 640 may be pushed distally away from under the ratchet arms 652, as a result of which the ratchet arms 652 may be free radially and may be moved elastically inward, as shown in FIGS. 24 and 25. The coupling sleeve 640 may thereby be released to rotate with respect to the housing, and may rotate relative to the housing during dispensing. Since the radial webs 651 and thus the ratchet arms 652 may be carried along by means of the openings 641 of the coupling sleeve 640, the ratchet arms 652 may move with the cams 653 over the grooves in the housing, and may thereby generate a tactile and/or acoustic click signal during dispensing.

LIST OF REFERENCE SIGNS

| | | |
|---|---|---|
| 1 injector | 48 webs | 173 angled section |
| 10 housing | 50 holding element | 174 tabs |
| 11 protective cap | 51 distal portion | 220 button insert |
| 12 carpule | 52 proximal portion | 230 dosing sleeve |
| 13 stopper | 53 cam | 231 saw teeth |
| 15 carpule holder | 54 grooves | 240 coupling sleeve |
| 20 housing insert | 60 drive sleeve | 246 end element |
| 21 recess | 61 webs | 250 click sleeve |
| 22 opening | 62 groove | 251 saw teeth |
| 23 ribs | 63 ratchet arms | 270 click disk |
| 24 bead | 70 click disk | 271 saw teeth |
| 25 saw teeth | 71 proximal arms | 272 saw teeth |
| 26 cam | 72 distal arms | 280 click spring |
| 27 inner thread | 75 stop nut | 290 release button |
| 28 inner thread | 76 webs | 330 dosing sleeve |
| 30 dosing sleeve | 80 piston rod | 331 teeth |
| 31 knob | 81 shoulder | 340 coupling sleeve |
| 32 grooves | 82 termination | 341 arm |

-continued

LIST OF REFERENCE SIGNS

| | | |
|---|---|---|
| 33 collar | 85 flange | 342 outward extension |
| 34 web | 90 release button | 430 dosing sleeve |
| 35 shoulder | 91 axial pin-shaped | 431 flexible arm |
| 36 saw teeth | formation | 520 distal housing insert |
| 37 bead | 92 collar | 522 opening |
| 38 stop sleeve | 130 dosing sleeve | 523 rib |
| 40 coupling sleeve | 131 teeth | 525 saw teeth |
| 41 teeth | 140 coupling sleeve | 527 inner thread |
| 42 cylindrical portion | 141 flange | 529 proximal housing |
| 43 external thread | 170 click disk | insert |
| 44 connecting webs | 171 point | 640 coupling sleeve |
| 45 flange | 172 half | 641 opening |
| 46 end portion | | 642 collar |
| 47 saw teeth | | 650 holding element |
| 39 external thread | | 651 radial web |
| 55 opening | | 652 ratchet arm |
| | | 653 cam |

What is claimed is:

1. A dosing device for an injection apparatus for dispensing a dose of a product, comprising:
a housing having a longitudinal axis;
a dose setting element configured as a dosing sleeve for setting the dose;
a holding element, wherein the holding element is coupled to the dosing sleeve such that the holding element and the dosing sleeve are rotatable but axially fixed relative to each other; and
a coupling sleeve for driving a drive device to dispense the dose, wherein at least a portion of the dose setting element, the holding element, and the coupling sleeve are arranged in the housing,
wherein for setting and correcting the dose, the dosing sleeve, the holding element and the coupling sleeve are configured to be moved relative to the housing in the direction of the longitudinal axis, and the coupling sleeve is configured to be held in a rotationally fixed manner relative to the housing by the holding element,
wherein for dispensing the dose, the coupling sleeve is releasable by the holding element, such that the coupling sleeve is rotatable relative to the housing, and
wherein the housing comprises a guide in which the holding element is displaceable along the longitudinal axis relative to the housing during the setting and correction of the dose, such that the holding element is guided in a rotationally fixed manner relative to the housing.

2. The dosing device according to claim 1, wherein to dispense the dose, the coupling sleeve is releasable by the holding element by a displacement of the coupling sleeve relative to the holding element along the longitudinal axis.

3. The dosing device according to claim 2, wherein the displacement of the coupling sleeve enables the coupling sleeve to be coupled to the dose setting element in a rotationally fixed manner.

4. The dosing device according to claim 3, wherein the coupling sleeve is coupleable to the dose setting element in a rotationally fixed manner by a toothed engagement.

5. The dosing device according to claim 1, wherein the coupling sleeve is configured to be held in a rotationally fixed manner relative to the holding element by a toothed engagement.

6. The dosing device according to claim 1, wherein the guide comprises a groove, and the holding element is guided in the groove in a rotationally fixed manner relative to the housing by a cam.

7. The dosing device according to claim 1, wherein the holding element defines an opening in which the coupling sleeve is received.

8. The dosing device according to claim 1, further comprising an elastic element configured to bias the coupling sleeve via a biasing force in a dosing position in which the coupling sleeve is held in a rotationally fixed manner relative to the holding element.

9. The dosing device according to claim 8, wherein the elastic element comprises a base body with at least two elastic arms, wherein the base body is oriented in a plane perpendicular to the longitudinal axis, wherein a first of the at least two arms points in a proximal direction of the dosing device, and a second of the at least two arms points in a distal direction of the dosing device.

10. The dosing device according to claim 9, wherein the dose setting element comprises teeth, and the coupling sleeve comprises teeth, wherein the first of the at least two arms of the elastic element slides over the teeth of the dose setting element or over the teeth of the coupling sleeve to generate an acoustic or tactile signal.

11. The dosing device according to claim 8, wherein the dose setting element and the coupling sleeve each comprise a flange in a proximal region, and the elastic element is arranged between the flanges.

12. The dosing device according to claim 1, further comprising a housing insert, the housing insert comprising a recess which forms the guide for guiding the holding element.

13. The dosing device according to claim 12, wherein the housing insert comprises an internal thread with which the dose setting element is threadedly engaged.

14. An injection device for dispensing a dose, the injection device comprising:
a carpule holder for holding a carpule with a medicinal substance;
a needle or cannula; and
a dosing device, the dosing device comprising:
a housing having a longitudinal axis;
a dose setting element configured as a dosing sleeve for setting the dose;
a holding element, wherein the holding element is coupled to the dosing sleeve such that the holding element and the dosing sleeve are rotatable but axially fixed relative to each other; and
a coupling sleeve for driving a drive device to dispense the dose, wherein at least a portion of the dose setting element, the holding element, and the coupling sleeve are arranged in the housing,
wherein for setting and correcting the dose, the dosing sleeve, the holding element and the coupling sleeve are movable relative to the housing in the direction of the longitudinal axis, and the coupling sleeve is configured to be held in a rotationally fixed manner relative to the housing by the holding element,
wherein for dispensing the dose, the coupling sleeve is releasable by the holding element, such that the coupling sleeve is rotatable relative to the housing, and
wherein the housing comprises a guide in which the holding element is displaceable along the longitudinal axis relative to the housing during the setting and correction of the dose, such that the holding element is guided in a rotationally fixed manner relative to the housing.

15. The injection device according to claim 14, further comprising an elastic element for biasing the coupling sleeve via a biasing force in a dosing position in which the coupling sleeve is held in the rotationally fixed manner relative to the holding element.

16. The injection device according to claim 15, wherein to dispense the dose, the coupling sleeve is releasable by the holding element out of the dosing position by a displacement of the coupling sleeve relative to the holding element along the longitudinal axis.

17. The injection device according to claim 15, wherein the dose setting element and the coupling sleeve each comprise a flange in a proximal region, and the elastic element is arranged between the flanges.

18. A dosing device for an injection apparatus for dispensing a dose of a product, comprising:
- a housing having a longitudinal axis;
- a dose setting element configured as a dosing sleeve for setting the dose;
- a holding element, wherein the holding element is coupled to the dosing sleeve such that the holding element and the dosing sleeve are rotatable but axially fixed relative to each other; and
- a coupling sleeve for driving a drive device to dispense the dose,
- wherein for setting and correcting the dose, the dosing sleeve, the holding element and the coupling sleeve are movable relative to the housing in the direction of the longitudinal axis, and the coupling sleeve is configured to be held in a rotationally fixed manner relative to the housing by the holding element,
- wherein for dispensing the dose, the coupling sleeve is releasable by the holding element by a displacement of the coupling sleeve relative to the holding element along the longitudinal axis, such that the coupling sleeve is rotatable relative to the housing, and
- wherein the housing comprises a guide in which the holding element is displaceable along the longitudinal axis relative to the housing during the setting and correction of the dose, such that the holding element is guided in a rotationally fixed manner relative to the housing.

19. The injection device according to claim 18, further comprising an elastic element for biasing the coupling sleeve via a biasing force in a dosing position in which the coupling sleeve is held in the rotationally fixed manner relative to the holding element, wherein the dose setting element and the coupling sleeve each comprise a flange in a proximal region, and the elastic element is arranged between the flanges.

* * * * *